(12) United States Patent
Kleemann et al.

(10) Patent No.: US 6,369,236 B1
(45) Date of Patent: Apr. 9, 2002

(54) IMIDAZOLE DERIVATIVES WITH BIPHENYLSULFONYL SUBSTITUTION METHOD FOR PREPARING THEM AND THEIR USE AS A DRUG OR DIAGNOSTIC AGENT

(75) Inventors: Heinz-Werner Kleemann, Bischofsheim; Hans Jochen Lang, Hofheim; Jan-Robert Schwark, Kelkheim; Stefan Petry, Frankfurt; Andreas Weichert, Egelsbach, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/743,957

(22) PCT Filed: Jul. 10, 1999

(86) PCT No.: PCT/EP99/04887

§ 371 Date: Jan. 18, 2001

§ 102(e) Date: Jan. 18, 2001

(87) PCT Pub. No.: WO00/03996

PCT Pub. Date: Jan. 27, 2000

(30) Foreign Application Priority Data

Jul. 18, 1998 (DE) .......................................... 198 32 428

(51) Int. Cl.[7] ................. C07D 233/70; C07D 233/88; A61K 31/4164
(52) U.S. Cl. .............. 548/336.5; 548/322.5; 548/334.5; 514/400; 514/821
(58) Field of Search .................... 548/336.5, 322.5, 548/334.5; 514/400, 821

(56) References Cited

U.S. PATENT DOCUMENTS

| 5,310,929 A | * | 5/1994 | Ardeccky et al. ............ 548/253 |
| 5,391,732 A | * | 2/1995 | Bhatnagar et al. .......... 540/603 |
| 5,482,957 A | * | 1/1996 | Wagner et al. ............... 514/398 |
| 5,527,919 A | | 6/1996 | Bhatnagar et al. |
| 5,604,251 A | * | 2/1997 | Heitsch et al. ............... 514/396 |
| 5,708,034 A | * | 1/1998 | Kleeman et al. ............. 514/618 |
| 5,807,878 A | | 9/1998 | Corbier et al. |
| 5,811,445 A | | 9/1998 | Corbier et al. |
| 5,977,155 A | | 11/1999 | Corbier et al. |

FOREIGN PATENT DOCUMENTS

| EP | 0479479 A1 | * | 8/1992 |
| EP | 0 648 763 A1 | | 4/1995 |
| EP | 0 855 392 A2 | | 7/1998 |
| WO | WO-92/20662 | * | 11/1992 |
| WO | WO 95/23791 | | 9/1995 |
| WO | WO 95/23792 | | 9/1995 |
| WO | WO 00/03994 | | 1/2000 |
| WO | WO 00/03996 | | 1/2000 |

OTHER PUBLICATIONS

Manfred Baumgarth et al., (2–Methyl– 5–(methylsulfonyl-)benzoyl)guanidine $Na^+/H^+$ Antiporter Inhibitors; J. Med. Chem., 1997, 40, 2017–2034.
Richard W. Brown; A Convenient Method for the Preparation of (Alkylsulfonyl)benzoic Acids, J. Org. Chem., 1991, 56, 4974–4976.
Derwent Abstract of WO 95/23791.
Derwent Abstract of EP 0 648 763.
Derwent Abstract of EP 0 855 392.
Derwent Abstract of WO 95/23792.
Derwent Abstract of WO 00/03994.
Derwent Abstract of WO 00/03996.

* cited by examiner

*Primary Examiner*—Floyd D. Higel
*Assistant Examiner*—Kamal Saeed
(74) *Attorney, Agent, or Firm*—Finnegan, Henderson, Farabow, Garrett & Dunner, LLP

(57) ABSTRACT

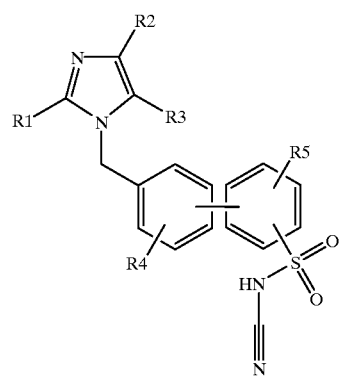

The invention relates to compounds of formula (I), wherein the symbols have the meanings indicated in the specification. The inventive compounds exhibit dramatic antiarrhythmic proprieties and contain a cardioprotective compound. They can preventively inhibit or strongly reduce pathophysiologic processes upon occurrence of ischemic injuries, especially ischemic cardiac arrhythmia. Said compounds also exhibit a strong inhibiting effect on cellular proliferation.

18 Claims, No Drawings

IMIDAZOLE DERIVATIVES WITH BIPHENYLSULFONYL SUBSTITUTION METHOD FOR PREPARING THEM AND THEIR USE AS A DRUG OR DIAGNOSTIC AGENT

This application is a national stage filing under 35 U.S.C. §371 of international application no. PCT/EP99/04887, filed Jul. 10, 1999.

The invention relates to compounds of the formula I

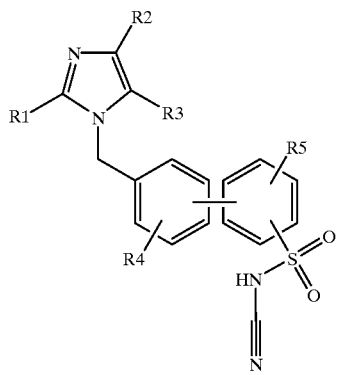

in which the symbols have the following meaning:

R(1) is hydrogen, alkyl having 1, 2, 3, 4, 5, 6, 7 or 8 carbon atoms or —$C_aH_{2a}$-phenyl, where the phenyl moiety is unsubstituted or substituted by 1, 2 or 3 identical or different radicals from the group consisting of F, Cl, Br, I, $CF_3$, methyl, methoxy, hydroxyl or NR(8)R(9);

R(8) and R(9) independently of one another are hydrogen or alkyl having 1, 2, 3 or 4 carbon atoms;

a is zero, 1 or 2; or

R(1) is —$C_bH_{2b}$-heteroaryl having 1, 2, 3, 4, 5, 6, 7, 8 or 9 carbon atoms, where the heteroaryl moiety is unsubstituted or substituted by 1, 2 or 3 identical or different radicals from the group consisting of F, Cl, Br, I, $CF_3$, methyl, methoxy, hydroxyl or NR(10)R(11);

R(10) and R(11) independently of one another are hydrogen or alkyl having 1, 2, 3 or 4 carbon atoms;

b is zero, 1 or 2; or

R(1) is —$C_dH_{2d}$-cycloalkyl having 3, 4, 5, 6 or 7 carbon atoms;

d is zero, 1 or 2;

R(2) and R(3) independently of one another are hydrogen, F, Cl, Br, I, $CF_3$, —CN, —$NO_2$, $CH_2OR(17)$, CO—R(6), O—R(7), O-(alkylene having 2, 3 or 4 carbon atoms)-O—R(17) or NR(50)R(51);

R(17) is hydrogen or alkyl having 1, 2, 3, 4, 5, 6, 7 or 8 carbon atoms;

R(6) is hydrogen, alkyl having 1, 2, 3, 4, 5, 6, 7 or 8 carbon atoms, OR(30) or phenyl which is unsubstituted or substituted by 1, 2 or 3 identical or different radicals from the group consisting of F, Cl, Br, I, $CF_3$, methyl, methoxy, hydroxyl or NR(31)R(32);

R(31) and R(32) independently of one another are hydrogen or alkyl having 1, 2, 3 or 4 carbon atoms;

R(30) is hydrogen or alkyl having 1, 2, 3, 4, 5, 6, 7 or 8 carbon atoms;

R(50) and R(51) independently of one another are -(alkylene having 2, 3 or 4 carbon atoms)-O—R(52);

R(52) is hydrogen or alkyl having 1, 2, 3, 4, 5, 6, 7 or 8 carbon atoms;

R(7) is hydrogen, alkyl having 1, 2, 3, 4, 5, 6, 7 or 8 carbon atoms, or phenyl, which is unsubstituted or substituted by 1, 2 or 3 identical or different radicals from the group consisting of F, Cl, Br, I, $CF_3$, methyl, methoxy, hydroxyl or NR(12)R(13);

R(12) and R(13) independently of one another are hydrogen or alkyl having 1, 2, 3 or 4 carbon atoms; or R(7) is heteroaryl having 1, 2, 3, 4, 5, 6, 7, 8 or 9 carbon atoms, which is unsubstituted or substituted by 1, 2 or 3 identical or different radicals from the group consisting of F, Cl, Br, I, $CF_3$, methyl, methoxy, hydroxyl or NR(14)R(15);

R(14) and R(15) independently of one another are hydrogen or alkyl having 1, 2, 3 or 4 carbon atoms; or R(2) and R(3) independently of one another are alkyl having 1, 2, 3, 4, 5, 6, 7 or 8 carbon atoms, cycloalkyl having 3, 4, 5, 6 or 7 carbon atoms or —$C_gH_{2g}$-phenyl, where the phenyl moiety is unsubstituted or substituted by 1, 2 or 3 identical or different radicals from the group consisting of F, Cl, Br, I, $CF_3$, methyl, methoxy, hydroxyl or NR(18)R(19);

R(18) and R(19) independently of one another are hydrogen or alkyl having 1, 2, 3 or 4 carbon atoms;

g is zero, 1 or 2; or

R(2) and R(3) independently of one another are —$C_lH_{2l}$-heteroaryl having 1, 2, 3, 4, 5, 6, 7, 8 or 9 carbon atoms, where the heteroaryl moiety is unsubstituted or substituted by 1, 2 or 3 identical or different radicals from the group consisting of F, Cl, Br, I, $CF_3$, methyl, methoxy, hydroxyl or NR(20)R(21);

R(20) and R(21) independently of one another are hydrogen or alkyl having 1, 2, 3 or 4 carbon atoms;

l is zero, 1 or 2; or

R(2) and R(3) independently of one another are $SO_n$—R(22);

n is zero, 1 or 2;

R(22) is alkyl having 1, 2, 3, 4, 5, 6, 7 or 8 carbon atoms, cycloalkyl having 3, 4, 5, 6 or 7 carbon atoms or —$C_sC_{2s}$-phenyl which is unsubstituted or substituted by 1, 2 or 3 identical or different radicals from the group consisting of F, Cl, Br, I, $CF_3$, methyl, methoxy, hydroxyl or NR(34)R(35);

R(34) and R(35) independently of one another are hydrogen or alkyl having 1, 2, 3 or 4 carbon atoms;

s is zero, 1 or 2;

R(4) and R(5) independently of one another are hydrogen, alkyl having 1, 2, 3, 4, 5, 6, 7 or 8 carbon atoms, F, Cl, Br, I, $CF_3$, —CN, —$NO_2$, $SO_p$—R(16), CO—R(23), O—R(24) or O-(alkylene having 2, 3 or 4 carbon atoms)-O—R(33);

p is zero, 1 or 2;

R(16) is alkyl having 1, 2, 3, 4, 5, 6, 7 or 8 carbon atoms or phenyl, which is unsubstituted or substituted by 1, 2 or 3 identical or different radicals from the group consisting of F, Cl, Br, I, $CF_3$, methyl, methoxy, hydroxyl or NR(26)R(27);

R(26) and R(27) independently of one another are hydrogen or alkyl having 1, 2, 3 or 4 carbon atoms;

R(23) is hydrogen, alkyl having 1, 2, 3, 4, 5, 6, 7 or 8 carbon atoms or OR(25);

R(25) is hydrogen, alkyl having 1, 2, 3, 4, 5, 6, 7 or 8 carbon atoms;

R(24) is hydrogen, alkyl having 1, 2, 3, 4, 5, 6, 7 or 8 carbon atoms or phenyl, which is unsubstituted or substituted by 1, 2 or 3 identical or different radicals from the group consisting of F, Cl, Br, I, $CF_3$, methyl, methoxy, hydroxyl or NR(28)R(29);

R(28) and R(29) independently of one another are hydrogen or alkyl having 1, 2, 3 or 4 carbon atoms;

R(33) is hydrogen or alkyl having 1, 2, 3, 4, 5, 6, 7 or 8 carbon atoms;

or their physiologically tolerable salts;

with the proviso that at least one of the radicals R(2) or R(3) is O-(alkylene having 2, 3 or 4 carbon atoms)-O—R(17) or NR(50)R(51).

Preferred compounds of the formula I are those in which:

R(1) is hydrogen, alkyl having 1, 2, 3 or 4 carbon atoms or —$C_aH_{2a}$-phenyl, where the phenyl moiety is unsubstituted or substituted by 1 or 2 identical or different radicals from the group consisting of F, Cl, Br, $CF_3$, methyl, methoxy, hydroxyl or NR(8)R(9);

R(8) and R(9) independently of one another are hydrogen or methyl;

a is zero or 1; or

R(1) is heteroaryl having 1, 2, 3, 4, 5, 6, 7, 8 or 9 carbon atoms which is unsubstituted or substituted by a radical from the group consisting of F, Cl, Br, $CF_3$, $CH_3$, methoxy, hydroxyl or NR(10)R(11);

R(10) and R(11) independently of one another are hydrogen or methyl; or

R(1) is —$C_dH_{2d}$-cycloalkyl having 3, 4, 5, 6 or 7 carbon atoms;

d is zero or 1;

R(2) and R(3) independently of one another are hydrogen, F, Cl, Br, $CF_3$, —CN, —$NO_2$, $CH_2OR(17)$, CO—R(6), O—R(7), O-(alkylene having 2 or 3 carbon atoms)-O—R(17) or NR(50)R(51);

R(17) is hydrogen or alkyl having 1, 2, 3 or 4 carbon atoms;

R(6) is hydrogen, alkyl having 1, 2, 3 or 4 carbon atoms, OR(30) or phenyl, which is unsubstituted or substituted by 1 or 2 identical or different radicals from the group consisting of F, Cl, Br, $CF_3$, methyl, methoxy, hydroxyl or NR(31)R(32);

R(31) and R(32) independently of one another are hydrogen or methyl;

R(30) is hydrogen or alkyl having 1, 2, 3 or 4 carbon atoms;

R(7) is hydrogen, alkyl having 1, 2, 3 or 4 carbon atoms or phenyl, which is unsubstituted or substituted by 1 or 2 identical or different radicals from the group consisting of F, Cl, Br, $CF_3$, methyl, methoxy, hydroxyl or NR(12)R(13);

R(12) and R(13) independently of one another are hydrogen or methyl; or

R(7) is heteroaryl having 1, 2, 3, 4, 5, 6, 7, 8 or 9 carbon atoms, which is unsubstituted or substituted by 1 or 2 identical or different radicals from the group consisting of F, Cl, Br, $CF_3$, methyl, methoxy, hydroxyl or NR(14)R(15);

R(14) and R(15) independently of one another are hydrogen or methyl;

R(50) and R(51) independently of one another are -(alkylene having 2 or 3 carbon atoms)-O—R(52);

R(52) is hydrogen or alkyl having 1, 2, 3 or 4 carbon atoms; or

R(2) and R(3) independently of one another are alkyl having 1, 2, 3 or 4 carbon atoms, cycloalkyl having 3, 4, 5, 6 or 7 carbon atoms or —$C_gH_{2g}$-phenyl, where the phenyl moiety is unsubstituted or substituted by 1 or 2 identical or different radicals from the group consisting of F, Cl, Br, $CF_3$, methyl, methoxy, hydroxyl or NR(18)R(19);

R(18) and R(19) independently of one another are hydrogen or methyl;

g is zero or 1; or

R(2) and R(3) independently of one another are heteroaryl having 1, 2, 3, 4, 5, 6, 7, 8 or 9 carbon atoms, which is unsubstituted or substituted by a radical from the group consisting of F, Cl, Br, $CF_3$, methyl, methoxy, hydroxyl or NR(20)R(21);

R(20) and R(21) independently of one another are hydrogen or methyl; or

R(2) and R(3) independently of one another are $SO_n$—R(22), n is zero, 1 or 2;

R(22) is alkyl having 1, 2, 3 or 4 carbon atoms, cycloalkyl having 3, 4, 5, 6 or 7 carbon atoms or —$C_sH_{2s}$-phenyl, where the phenyl moiety is unsubstituted or substituted by 1 or 2 identical or different radicals from the group consisting of F, Cl, Br, $CF_3$, methyl, methoxy, hydroxyl or NR(34)R(35);

R(34) and R(35) independently of one another are hydrogen or methyl;

s is zero or 1;

R(4) and R(5) independently of one another are hydrogen, alkyl having 1, 2, 3 or 4 carbon atoms, F, Cl, Br, $CF_3$, —CN, —$NO_2$, $SO_p$—R(16), CO—R(23), O—R(24) or O-(alkylene having 2 or 3 carbon atoms)-O—R(33);

p is zero, 1 or 2;

R(16) is alkyl having 1, 2, 3 or 4 carbon atoms or phenyl, which is unsubstituted or substituted by 1 or 2 identical or different radicals from the group consisting of F, Cl, Br, $CF_3$, methyl, methoxy, hydroxyl or NR(26)R(27);

R(26) and R(27) independently of one another are hydrogen or methyl;

R(23) is hydrogen, alkyl having 1, 2, 3 or 4 carbon atoms or OR(25);

R(25) is hydrogen or alkyl having 1, 2, 3 or 4 carbon atoms;

R(24) is hydrogen, alkyl having 1, 2, 3 or 4 carbon atoms or phenyl, which is unsubstituted or substituted by 1 or 2 identical or different radicals from the group consisting of F, Cl, Br, $CF_3$, methyl, methoxy, hydroxyl or NR(28)R(29);

R(28) and R(29) independently of one another are hydrogen or methyl;

R(33) is hydrogen or alkyl having 1, 2, 3 or 4 carbon atoms;

or their physiologically tolerable salts;

with the proviso that at least one of the radicals R(2) or R(3) is O-(alkylene having 2 or 3 carbon atoms)-O—R(17) or NR(50)R(51).

Particularly preferred compounds of the formula I are those in which:

R(1) is hydrogen, alkyl having 1, 2, 3 or 4 carbon atoms or phenyl, which is unsubstituted or substituted by a radical from the group consisting of F, Cl, Br, $CF_3$, methyl, methoxy, hydroxyl or NR(8)R(9);

R(8) and R(9) independently of one another are hydrogen or methyl; or

R(1) is heteroaryl having 1, 2, 3, 4, 5, 6, 7, 8 or 9 carbon atoms, which is unsubstituted or substituted by a radical from the group consisting of F, Cl, Br, CF$_3$, methyl, methoxy, hydroxyl or NR(10)R(11);
R(10) and R(11) independently of one another are hydrogen or methyl; or
R(1) is cycloalkyl having 3, 4, 5, 6 or 7 carbon atoms;
R(2) and R(3) independently of one another are hydrogen, F, Cl, Br, CF$_3$, —CN, —NO$_2$, CO—R(6), O—R(7), O—CH$_2$—CH$_2$—O—R(17) or NR(50)R(51);
R(6) is hydrogen, alkyl having 1, 2, 3 or 4 carbon atoms, OR(30) or phenyl, which is unsubstituted or substituted by a radical from the group consisting of F, Cl, Br, CF$_3$, methyl, methoxy, hydroxyl or NR(31)R(32);
R(31) and R(32) independently of one another are hydrogen or methyl;
R(30) is hydrogen or alkyl having 1, 2 or 3 carbon atoms:
R(7) is hydrogen, alkyl having 1, 2, 3 or 4 carbon atoms or phenyl, which is unsubstituted or substituted by a radical from the group consisting of F, Cl, Br, methyl, methyl, methoxy, hydroxyl or NR(12)R(13);
R(12) and R(13) independently of one another are hydrogen or methyl; or
R(7) is heteroaryl having 1, 2, 3, 4, 5, 6, 7, 8 or 9 carbon atoms, which is unsubstituted or substituted by a radical from the group consisting of F, Cl, Br, CF$_3$, methyl, methoxy, hydroxyl or NR(14)R(15);
R(14) and R(15) independently of one another are hydrogen or methyl;
R(17) is methyl or ethyl;
R(50) and R(51) independently of one another are —CH$_2$—CH$_2$—O—R(52); R(52) is methyl or ethyl; or
R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a radical from the group consisting of F, Cl, Br, CF$_3$, methyl, methoxy, hydroxyl or NR(18)R(19);
R(18) and R(19) independently of one another are hydrogen or methyl; or
R(2) and R(3) independently of one another are heteroaryl having 1, 2, 3, 4, 5, 6, 7, 8 or 9 carbon atoms, which is unsubstituted or substituted by a radical from the group consisting of F, Cl, Br, CF$_3$, CH$_3$, methoxy, hydroxyl or NR(20)R(21);
R(20) and R(21) independently of one another are hydrogen or methyl; or
R(2) and R(3) independently of one another are SO$_n$—R(22);
n is zero or 2;
R(22) is alkyl having 1, 2, 3 or 4 carbon atoms, cycloalkyl having 3, 4, 5, 6 or 7 carbon atoms or phenyl which is unsubstituted or substituted by 1 or 2 identical or different radicals from the group consisting of F, Cl, Br, CF$_3$, methyl, methoxy, hydroxyl or NR(34)R(35);
R(34) and R(35) independently of one another are hydrogen or methyl;
R(4) and R(5) independently of one another are hydrogen, alkyl having 1, 2, 3 or 4 carbon atoms, F, Cl, CF$_3$, —CN, —NO$_2$, SO$_p$—R(16), CO—R(23), O—R(24) or O—CH$_2$—CH$_2$—O—R(33);
p is zero or 2;
R(23) is hydrogen, alkyl having 1, 2, 3 or 4 carbon atoms or OR(25);

R(25) is hydrogen or alkyl having 1, 2 or 3 carbon atoms;
R(24) is hydrogen, alkyl having 1, 2, 3 or 4 carbon atoms or phenyl, which is unsubstituted or substituted by a radical from the group consisting of F, Cl, Br, CF$_3$, methyl, methoxy, hydroxyl or NR(28)R(29);
R(28) and R(29) independently of one another are hydrogen or methyl;
R(16) is alkyl having 1, 2, 3 or 4 carbon atoms or phenyl which is unsubstituted or substituted by a radical from the group consisting of F, Cl, Br, CF$_3$, methyl, methoxy, hydroxyl or NR(26)R(27);
R(26) and R(27) independently of one another are hydrogen or methyl;
R(33) is methyl or ethyl; or their physiologically tolerable salts;
with the proviso that at least one of the radicals R(2) or R(3) is O—CH$_2$—CH$_2$—O—R(17) or NR(50)R(51).
Very particularly preferred compounds of the formula I are those in which:
R(1) is alkyl having 1, 2, 3 or 4 carbon atoms or phenyl which is unsubstituted or substituted by a radical from the group consisting of F, Cl, CF$_3$, methyl or methoxy; or
R(1) is heteroaryl having 1, 2, 3, 4, 5, 6, 7, 8 or 9 carbon atoms, which is unsubstituted or substituted by a radical from the group consisting of F, Cl, CF$_3$, methyl or methoxy; or
R(1) is cycloalkyl having 3, 4, 5, 6 or 7 carbon atoms;
R(2) and R(3) independently of one another are hydrogen, F, Cl, CF$_3$, —CN, CO—R(6), O—R(7), O—CH$_2$—CH$_2$—O—CH$_3$CH$_3$or NR(50)R(51);
R(6) is hydrogen, alkyl having 1, 2, 3 or 4 carbon atoms, OR(30) or phenyl, which is unsubstituted or substituted by a radical from the group consisting of F, Cl, CF$_3$, methyl or methoxy;
R(30) is hydrogen, methyl or ethyl;
R(7) is hydrogen, alkyl having 1, 2, 3 or 4 carbon atoms or phenyl, which is unsubstituted or substituted by a radical from the group consisting of F, Cl, CF$_3$, methyl or methoxy; or
R(7) is heteroaryl having 1, 2, 3, 4, 5, 6, 7, 8 or 9 carbon atoms, which is unsubstituted or substituted by a radical from the group consisting of F, Cl, Br, CF$_3$, methyl or methoxy;
R(50) and R(51) are —CH$_2$—CH$_2$—O—CH$_3$; or
R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a radical from the group consisting of F, Cl, CF$_3$, methyl and methoxy; or
R(2) and R(3) independently of one another are heteroaryl having 1, 2, 3, 4, 5, 6, 7, 8 or 9 carbon atoms, which is unsubstituted or substituted by a radical from the group consisting of F, Cl, CF$_3$, methyl or methoxy; or
R(2) and R(3) independently of one another are SO$_n$—R(22);
n is zero or 2;
R(22) is alkyl having 1, 2, 3 or 4 carbon atoms or phenyl which is unsubstituted or substituted by 1 or 2 identical or different radicals from the group consisting of F, Cl, CF$_3$, methyl or methoxy;
R(4) and R(5) independently of one another are hydrogen, methyl, F, Cl, CF$_3$, —CN, SO$_2$—R(16), CO—R(23), O—R(24) or O—CH$_2$—CH$_2$—O—CH$_3$;

R(16) is alkyl having 1, 2, 3 or 4 carbon atoms or phenyl which is unsubstituted or substituted by a radical from the group consisting of F, Cl, CF$_3$, methyl or methoxy;

R(23) is hydrogen, methyl or OR(25); R(25) is hydrogen, methyl or ethyl;

R(24) is hydrogen, alkyl having 1, 2, 3 or 4 carbon atoms or phenyl, which is unsubstituted or substituted by a radical from the group consisting of F, Cl, CF$_3$, methyl or methoxy;

or their physiologically tolerable salts;

In addition, preferred compounds are those in which:

R(1) is alkyl having 1, 2, 3, 4, 5, 6, 7 or 8 carbon atoms, —C$_d$H$_{2d}$-cycloalkyl having 3, 4, 5, 6 or 7 carbon atoms where d is equal to zero, 1 or 2 or —C$_a$H$_{2a}$-phenyl, where the phenyl moiety is unsubstituted or substituted by 1, 2 or 3 identical or different radicals from the group consisting of F, Cl, Br, I, CF$_3$, methyl, methoxy, hydroxyl or NR(8)R(9);

R(8) and R(9) independently of one another are hydrogen or alkyl having 1, 2, 3 or 4 carbon atoms;

a is zero, 1 or 2;

R(2) is O-(alkylene having 2, 3 or 4 carbon atoms)-O—R(17) or NR(50)R(51);

R(17) is hydrogen or alkyl having 1, 2, 3, 4, 5, 6, 7 or 8 carbon atoms;

R(50) and R(51) independently of one another are -(alkylene having 2, 3 or 4 carbon atoms)-O—R(52);

R(52) is hydrogen or alkyl having 1, 2, 3, 4, 5, 6, 7 or 8 carbon atoms;

R(3) is hydrogen, —CN or CO—R(6);

R(6) is hydrogen, alkyl having 1, 2, 3, 4, 5, 6, 7 or 8 carbon atoms or OR(30);

R(30) is hydrogen or alkyl having 1, 2, 3, 4, 5, 6, 7 or 8 carbon atoms;

R(4) is hydrogen, Cl, F, Br, I, SO$_p$—R(16) or O—CH$_2$—CH$_2$—O—R(33);

p is zero, 1 or 2;

R(16) is alkyl having 1, 2, 3, 4, 5, 6, 7 or 8 carbon atoms or phenyl which is unsubstituted or substituted by 1, 2 or 3 identical or different radicals from the group consisting of F, Cl, Br, I, CF$_3$, methyl, methoxy, hydroxyl or NR(26)R(27);

R(26) and R(27) independently of one another are hydrogen or alkyl having 1, 2, 3 or 4 carbon atoms;

R(33) is methyl or ethyl;

(5) is hydrogen;

or their physiologically tolerable salts.

Preferred compounds are also those in which:

R(1) is —C$_a$H$_{2a}$-phenyl, where the phenyl moiety is unsubstituted or substituted by 1 or 2 identical or different radicals from the group consisting of F, Cl, Br, CF$_3$, methyl, methoxy, hydroxyl or NR(8)R(9);

R(8) and R(9) independently of one another are hydrogen or methyl;

a is zero or 1;

R(2) is O—(alkylene having 2, 3 or 4 carbon atoms)—O—R(17) or NR(50)R(51);

R(17) is alkyl having 1, 2, 3 or 4 carbon atoms, in particular methyl;

R(50) and R(51) independently of one another are -(alkylene having 2, 3 or 4 carbon atoms)-O—R(52);

R(52) is alkyl having 1, 2, 3 or 4 carbon atoms, in particular methyl;

R(3) is CO—R(6);

R(6) is hydrogen;

R(4) is SO$_2$R(16) where R(16) is alkyl having 1, 2, 3 or 4 carbon atoms, in particular methyl or O—CH$_2$—CH$_2$—O—CH$_3$;

R(5) is hydrogen;

and their physiologically tolerable salts.

Particularly preferred compounds of the formula I are those in which R(2) is O—CH$_2$—CH$_2$—O—R(17) or NR(50)R(51) where R(17) is equal to alkyl having 1, 2, 3 or 4 carbon atoms, in particular methyl and R(50) and R(51) is equal to —CH$_2$—CH$_2$—O—R(52) where R(52) is equal to alkyl having 1, 2, 3 or 4 carbon atoms, in particular methyl; and R(1), R(3), R(4) and R(5) are as defined above, and their physiologically tolerable salts.

In addition, preferred compounds of the formula I are also those in which radicals R(1), R(2), R(3), R(4) and R(5) are as defined above and the biphenyl substituent is linked as in formula Ia, Ib, Ic, Id, Ie, If, Ig, Ih or Ii, preferably as in formula I, Ia

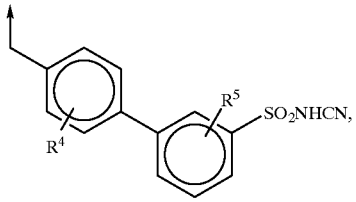

Ib

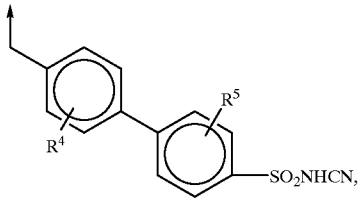

Ic

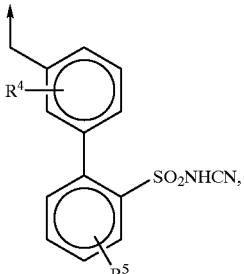

Id

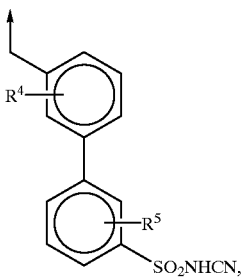

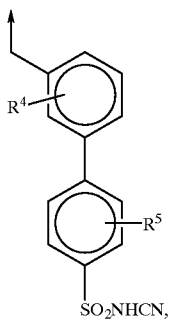

Ie

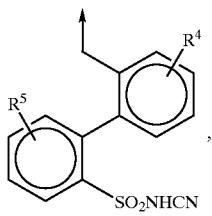

If

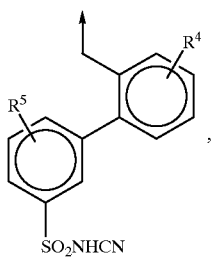

Ig

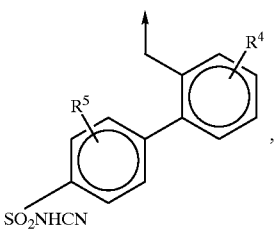

Ih

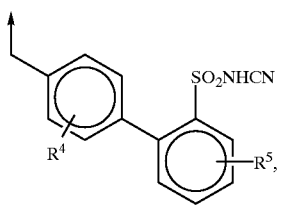

Ii

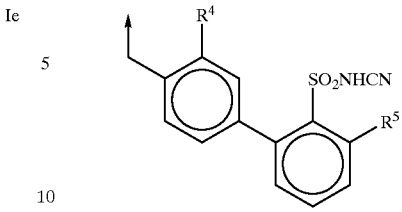

Ij and their physiologically tolerable salts.

In addition, preferred compounds of the formula I are those in which the radicals R(1), R(2), R(3), R(4) and R(5) are as defined above and the radicals R(4) and R(5) as in the formula Ij are linked to the biphenyl substituent and their physiologically tolerable salts.

Alkyl radicals and alkylene radicals can be straight-chain or branched. This also applies to the alkylene radicals of the formulae $C_aH_{2a}$, $C_bH_{2b}$, $C_dH_{2d}$, $C_gH_{2g}$ and $C_lH_{2l}$. Alkyl radicals and alkylene radicals can also be straight-chain or branched if they are substituted or are contained in other radicals, e.g. in an alkoxy radical or in an alkylmercapto radical or in a fluorinated alkyl radical.

Cycloalkyl is also understood as meaning alkyl-substituted rings.

Examples of alkyl radicals having 1, 2, 3, 4, 5, 6, 7 or 8 carbon atoms are: methyl, ethyl, n-propyl, n-butyl, pentyl, hexyl, heptyl, octyl, isopropyl, isobutyl, isopentyl, neopentyl, isohexyl, 3-methylpentyl, sec-butyl, tert-butyl, tert-pentyl. The divalent radicals derived from these radicals, e.g. methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc. are examples of alkylene radicals.

Cycloalkyl radicals having 3, 4, 5, 6 or 7 carbon atoms are in particular cyclopropyl, cyclobutyl, cyclopentyl, cyclohexyl, cycloheptyl, which, however, can also be substituted, for example, by alkyl having 1, 2, 3 or 4 carbon atoms. Examples of substituted cycloalkyl radicals which may be mentioned are 4-methylcyclohexyl and 2,3-dimethylcyclopentyl.

Heteroaryl having 1, 2, 3, 4, 5, 6, 7, 8 or 9 carbon atoms is understood as meaning in particular radicals which are derived from phenyl or naphthyl, in which one or more CH groups are replaced by N and/or in which at least two adjacent CH groups are replaced by S, NH or O (with formation of a five-membered aromatic ring). In addition, one or both atoms of the condensation site of bicyclic radicals (such as in indolizinyl) can also be nitrogen atoms.

Heteroaryl is in particular furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl, cinnolinyl. N-Containing heterocycles having 1, 2, 3, 4, 5, 6, 7, 8 or 9 carbon atoms are in particular the aromatic systems 1-, 2- or 3-pyrrolyl, 1-, 2-, 4- or 5-imidazolyl, 1-, 3-, 4-or 5-pyrazolyl, 1,2,3-triazol-1-, -4- or 5-yl, 1,2,4-triazol-1, -3- or -5-yl, 1- or 5-tetrazolyl, 2-, 4- or 5-oxazolyl, 3-, 4- or 5-isoxazolyl, 1,2,3-oxadiazol-4- or 5-yl, 1,2,4-oxadiazol-3- or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3-or -5-yl, 1,2,3-thiadiazol-4- or 5-yl, 2-, 3- or 4-pyridyl, 2-, 4-, 5-or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6-, 7- or 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

The N-containing heterocycles pyrrolyl, imidazolyl, quinolyl, pyrazolyl, pyridyl, pyrazinyl, pyrimidinyl and pyridazinyl are particularly preferred. Thienyl is both 2- and 3-thienyl. Furyl is 2- and 3-furyl.

Monosubstituted phenyl radicals can be substituted in the 2-, the 3- or the 4-position, disubstituted in the 2,3-, 2,4-, 2,5-, 2,6-, 3,4 or 3,5-position, trisubstituted in the 2,3,4-, 2,3,5-, 2,3,6- 2,4,5-, 2,4,6- or 3,4,5-position. The same correspondingly applies analogously to the N-containing heterocycles or the thiophene radical. In the case of di- or trisubstitution of a radical, the substituents can be identical or different.

If the compounds of the formula I contain one or more acidic or basic groups or one or more basic heterocycles, the invention also relates to the corresponding physiologically or toxicologically tolerable salts, in particular the pharmaceutically utilizable salts. Thus the compounds of the formula I which carry acidic groups, e.g. one or more COOH groups, can be used, for example, as alkali metal salts, preferably sodium or potassium salts, or as alkaline earth metal salts, e.g. calcium or magnesium salts, or as ammonium salts, e.g. as salts with ammonia or organic amines or amino acids. Compounds of the formula I which carry one or more basic, i.e. protonatable, groups or contain one or more basic heterocyclic rings can also be used in the form of their physiologically tolerable acid addition salts with inorganic or organic acids, for example as hydrochlorides, phosphates, sulfates, methanesulfonates, acetates, lactates, maleates, fumarates, malates, gluconates etc.

If the compounds of the formula I simultaneously contain acidic and basic groups in the molecule, the invention also includes, in addition to the salt forms described, internal salts, so-called betaines. Salts can be obtained from the compounds of the formula I by customary processes, for example by combination with an acid or base in a solvent or dispersant or alternatively from other salts by anion exchange. Physiologically tolerable salts of compounds of the formula (I) are also understood as meaning, for example, organic and inorganic salts, such as are described in Remington's Pharmaceutical Sciences (17th edition, pages 1418 (1985)). On account of the physical and chemical stability and the solubility, sodium, potassium, calcium and ammonium salts, inter alia, are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

If appropriately substituted, the compounds of the formula I can be present in stereoisomeric forms. If the compounds of the formula I contain one or more asymmetric centers, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to, for example, enantiomers in enantiomerically pure form, both as levo- and dextrorotatory antipodes, and in the form of mixtures of the two enantiomers in different ratios or in the form of racemates. In the case of the presence of cis/trans isomerism, the invention relates both to the cis form and the trans form and mixtures of these forms. If desired, the individual stereoisomers can be prepared by resolution of a mixture according to customary methods or, for example, by stereoselective synthesis. In the case of the presence of mobile hydrogen atoms, the present invention also includes all tautomeric forms of the compounds of the formula I.

The invention also relates to a process for the preparation of the compounds of the formula I, and their physiologically tolerable salts, which comprises reacting a compound of the formula II

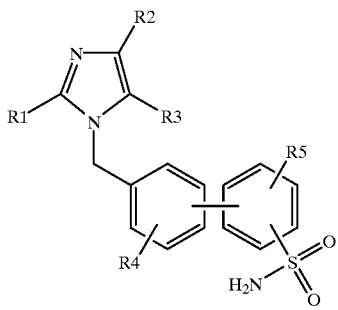

in which the radicals are as defined above and which, analogously to J. Med. Chem. 1995, 38, 2357 can be prepared in a manner known per se, with cyanogen bromide. The reaction is advantageously carried out in a dipolar aprotic solvent which is stable to cyanogen bromide, for example acetonitrile, DMA, TMU or NMP, using a strong auxiliary base which is not very nucleophilic, such as, for example, $K_2CO_3$ or $Cs_2CO_3$. A suitable reaction temperature is a temperature from 0° C. to the boiling point of the solvent used; a temperature from 60° C. to 120° C. is preferred.

The introduction of the substituents R(2) or R(3) equal to alkoxyalkoxy is carried out by nucleophilic aromatic substitution on compounds of the formula II where R(2) is equal to a nucleofugic leaving group, preferably F, Cl or Br and R(3) is equal to formyl or on compounds of the formula II where R(3) is equal to a nucleofugic leaving group, preferably F, Cl or Br and R(2) is equal to formyl. The nucleophile employed is advantageously an alkali metal salt of the alcohol concerned, the sodium, potassium or cesium salt is preferred, in the alcohol concerned as a solvent. The reaction temperature is a temperature between 0° C. and the boiling point of the alcohol; a temperature between 40° C. and the boiling point of the alcohol is preferred.

The introduction of the substituents R(2) or R(3) equal to bis(alkoxyalyl)amino is carried out by nucleophilic aromatic substitution on compounds of the formula II where R(2) is equal to a nucleofugic leaving group, preferably F, Cl or Br and R(3) is equal to formyl or on compounds of the formula II where R(3) is equal to a nucleofugic leaving group, preferably F, Cl or Br and R(2) is equal to formyl. The nucleophile employed is either the bis(alkoxyalyl)amine concerned or an alkali metal salt of the amine concerned, the lithium sodium, potassium or cesium salt is preferred, in a dipolar aprotic solvent. Suitable solvents are therefore THF, DMF, tetramethylurea, N-methylpyrrolidone and hexamethylphosphoramide. The reaction temperature is a temperature between 0° C. and the boiling point of the solvent; a temperature between 40° C. and the boiling point of the solvent is preferred.

The introduction of the substituent R(4) is advantageously carried out at the stage of the toluene derivative III

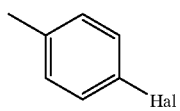

III where Hal is a leaving group compatible with the Suzuki reaction, preferably bromine or iodine. The introduction of an $SO_2$-alkyl radical by means of chlorosulfonation is described by way of example in J. Med. Chem. 1997, 40, 2017 or J. Org. Chem. (1991), 56(16), 4974–6.

All reactions for the synthesis of the compounds of the formula I are well known per se to the person skilled in the art and can be carried out under standard conditions according to or analogously to literature procedures, such as are described, for example, in Houben-Weyl, Methoden der organischen Chemie [Methods of organic chemistry], Thieme-Verlag, Stuttgart, or Organic Reactions, John Wiley & Sons, New York. Depending on the conditions in the individual case, it may also be advantageous or necessary in the synthesis of the compounds of the formula I, in order to avoid side reactions, to block certain functional groups temporarily by the introduction of protective groups and later to then release them again or to employ functional groups first in the form of precursors from which the desired functional group is generated in a later step. Such synthesis strategies and the protective groups or precursors suitable for the individual case are known to the person skilled in the art. The compounds of the formula I obtained can optionally be purified by customary purification methods, for example by recrystallization or chromatography. The starting compounds for the preparation of the compounds of the formula I are commercially obtainable or can be prepared by or analogously to literature procedures.

In addition, the invention relates to the use of a compound of the formula I and/or of a physiologically tolerable salt thereof for the production of a medicament for the treatment or prophylaxis of illnesses caused by ischemic conditions;

and also the use of a compound of the formula I and/or of a physiologically tolerable salt thereof for the production of a medicament for the treatment or prophylaxis of cardiac infarct;

and also the use of a compound of the formula I and/or of a physiologically tolerable salt thereof for the production of a medicament for the treatment or prophylaxis of angina pectoris;

and also the use of a compound of the formula I and/or of a physiologically tolerable salt thereof for the production of a medicament for the treatment or prophylaxis of ischemic conditions of the heart;

and also the use of a compound of the formula I and/or of a physiologically tolerable salt thereof for the production of a medicament for the treatment or prophylaxis of ischemic conditions of the peripheral and central nervous system and of stroke;

and also the use of a compound of the formula I and/or of a physiologically tolerable salt thereof for the production of a medicament for the treatment or prophylaxis of ischemic conditions of peripheral organs and limbs;

and also the use of a compound of the formula I and/or of a physiologically tolerable salt thereof for the production of a medicament for the treatment of states of shock;

and also the use of a compound of the formula I and/or of a physiologically tolerable salt thereof for the production of a medicament for use in surgical operations and organ transplantation;

and also the use of a compound of the formula I and/or of a physiologically tolerable salt thereof for the production of a medicament for the preservation and storage of transplants for surgical measures;

and also the use of a compound of the formula I and/or of a physiologically tolerable salt thereof for the production of a medicament for the treatment of illnesses in which cell proliferation is a primary or secondary cause; and thus their use for the production of an antiatherosclerotic, an agent against diabetic late complications, carcinomatous disorders, fibrotic disorders such as pulmonary fibrosis, hepatic fibrosis or renal fibrosis, or prostate hyperplasia;

and also the use of a compound of the formula I and/or of a physiologically tolerable salt thereof for the production of a medicament for the treatment of impaired respiratory drive;

and also a pharmaceutical preparation which comprises an efficacious amount of a compound of the formula I and/or of a physiologically tolerable salt thereof.

The compounds of the formula I according to the invention are suitable as inhibitors of the sodium-dependent bicarbonate/chloride exchanger (NCBE) or of the sodium/bicarbonate symporter.

Compounds similar to the compounds of the formula I according to the invention are disclosed in U.S. Pat. Nos. 5,482,957 and 5,604,251. However, they do not have the sulfonylcyanamide side chain which is always present according to the invention. Imidazole derivatives as angiotensin II antagonists are also described in WO9523792, WO9523791, U.S. Pat. No. 5,391,732, EP-A 648763. The known compounds are angiotensin II receptor antagonists of the subtype AT1, which action is not present or only present to a small extent in the compounds I according to the invention.

In the earlier European Patent Application EP-A 855392, imidazole derivatives having a biphenylsulfonylcyanamide side chain are proposed as NCBE inhibitors. The novel imidazole derivatives having a biphenylsulfonylcyanamide side chain described in the present invention have a specific substituent R(2) and/or R(3) on the imidazole ring and are distinguished by a high efficacy in the inhibition of the cellular $Na^+$-dependent bicarbonate/chloride exchange as well as an improved bioavailability.

The compounds of the formula (I) according to the invention exhibit very good antiarrhythmic properties, such as are important, for example, for the treatment of illnesses which occur in the case of oxygen deficiency symptoms. Because of their pharmacological properties, the compounds of the formula (I) are outstandingly suitable as antiarrhythmic pharmaceuticals having a cardioprotective component for infarct prophylaxis and infarct treatment and also for the treatment of angina pectoris, where they also preventively inhibit or greatly decrease the pathophysiological processes in the formation of ischemically induced damage, in particular in the elicitation of ischemically induced cardiac arrhythmias. Because of their protective actions against pathological hypoxic and ischemic situations, the compounds of the formula (I) according to the invention can be used, as a result of inhibition of the cellular $Na^+$-dependent $Cl^-/HCO_3^-$ exchange mechanism (NCBE) or of the sodium/bicarbonate symporter, as a pharmaceutical for the treatment of all acute or chronic damage caused by ischemia or illnesses induced primarily or secondarily thereby. They protect organs which have an acutely or chronically deficient supply of oxygen by reducing or preventing ischemically induced damage and are thus suitable as pharmaceuticals, for example in thromboses, vasospasms, atherosclerosis or in surgical interventions (e.g. in organ transplantation of the kidney and liver where the compounds can be used both for the protection of the organs in the donor before and during removal, for the protection of removed organs, for example, during treatment with or storage thereof in physiological bath fluids, and also during transfer to the recipient's body) or chronic or acute kidney failure.

The compounds of the formula (I) are also valuable pharmaceuticals having a protective action when carrying out angioplastic surgical interventions, for example on the heart and also on peripheral vessels. Corresponding to their protective action against ischemically induced damage, the compounds are also suitable as pharmaceuticals for the treatment of ischemias of the nervous system, in particular of the CNS, where they are suitable, for example, for the treatment of stroke or of cerebral edema.

Moreover, the compounds of the formula (I) according to the invention are also suitable for the treatment of forms of shock, such as, for example, of allergic, cardiogenic, hypovolemic and of bacterial shock.

Moreover, the compounds of the formula (I) according to the invention are distinguished by strong inhibitory action on the proliferation of cells, for example fibroblast cell proliferation and the proliferation of the vascular smooth muscle cells and of the mesangium cells. Therefore the compounds of the formula (I) are suitable as valuable therapeutics for illnesses in which cell proliferation is a primary or secondary cause, and can therefore be used as antiatherosclerotics, agents against diabetic late complications, carcinomatous disorders, fibrotic disorders such as pulmonary fibrosis, hepatic fibrosis or renal fibrosis, organ hypertrophs and/or hyperplasia, in particular in prostate hyperplasia or prostate hypertrophy.

The compounds of the formula I according to the invention and their physiologically tolerable salts are suitable for use in the therapy and/or propylaxis of cardiacinfarct, of angina pectoris, of illnesses caused by ischemic conditions, of disturbed respiratory drive, of ischemic conditions of the heart, of ischemic conditions of the peripheral and central nervous system and of stroke, of ischemic conditions of peripheral organs and limbs, of illnesses in which cell proliferation is a primary or secondary cause, or in the treatment of states of shock, or for use in surgical operations and organ transplantation or for the preservation and storage of transplants for surgical measures.

It was found that inhibitors of the $Na^+$-dependent $Cl^-$/$HCO_3^-$ exchanger (NCBE inhibitors) or of the sodium/bicarbonate symporter can stimulate the respiration by an increase in the chemosensitivity of the respiratory chemoreceptors. These chemoreceptors are responsible to a considerable extent for the maintenance of an ordered respiratory activity. They are activated by hypoxia, pH decrease and rise in $CO_2$ (hypercapnia) in the body and lead to an adjustment of the respiratory minute volume. During sleep, the respiration is particularly susceptible to disturbance and is dependent to a great extent on the activity of the chemoreceptors. Improvement in the respiratory drive by stimulation of the chemoreceptors with substances which inhibit $Na^+$-dependent $Cl^-$/$HCO_3^-$ exchange leads to an improvement in the respiration in the following clinical conditions and illnesses: disturbed central respiratory drive (e.g. central sleep apnea, cot death, postoperative hypoxia), muscle-related respiratory disorders, respiratory disorders after long-term ventilation, respiratory disorders during adaptation in a high mountain region, obstructive and mixed forms of sleep apneas, acute and chronic lung diseases with hypoxia and hypercapnia.

The compounds of the formula I according to the invention and their physiologically tolerable salts can be used in animals, preferably in mammals, and in particular in humans, as pharmaceuticals on their own, as mixtures with one another or in the form of pharmaceutical preparations. The present invention also relates to the compounds of the formula I and their physiologically tolerable salts for administration as pharmaceuticals, their use in the therapy and prophylaxis of the syndromes mentioned and their production of medicaments therefor. The present invention furthermore relates to pharmaceutical preparations which as active constituent contain an efficacious dose of at least one compound of the formula I and/or of a physiologically tolerable salt thereof in addition to customary pharmaceutically innocuous vehicles and excipients. The pharmaceutical preparations normally contain 0.1 to 99 percent by weight, preferably 0.5 to 95 percent by weight, of the compounds of the formula I and/or their physiologically tolerable salts. The pharmaceutical preparations can be produced in a manner known per se. For this, the compounds of the formula I and/or their physiologically tolerable salts are brought, together with one or more solid or liquid pharmaceutical vehicles and/or excipients and, if desired, in combination with other pharmaceutical active compounds, into a suitable administration form or dose form, which can then be used as a pharmaceutical in human or veterinary medicine.

Pharmaceuticals which contain a compound of the formula (I) and/or its physiologically tolerable salts can in this case be administered orally, parenterally, intravenously, rectally or by inhalation, the preferred manner of administration being dependent on the particular symptoms of the disorder. The compounds of the formula I can in this case be used on their own or together with pharmaceutical auxiliaries, namely both in veterinary and in human medicine.

Auxiliaries which are suitable for the desired pharmaceutical formulation are familar to the person skilled in the art on the basis of his expert knowledge. Beside solvents, gel-forming agents, suppository bases, tablet auxiliaries, and other vehicles, it is possible to use, for example, antioxidants, dispersants, emulsifiers, antifoams, flavor corrigents, preservatives, solubilizers or colorants.

For an oral administration form, the active compounds are mixed with the additives suitable therefor, such as excipients, stabilizers or inert diluents, and brought by the customary methods into the suitable administration forms, such as tablets, coated tablets, hard capsules, aqueous, alcoholic or oily solutions. Inert excipients which can be used are, for example, gum arabic, magnesia, magnesium carbonate, potassium phosphate, lactose, glucose or starch, in particular corn starch. In this case, the preparation can be realized both as dry and as moist granules. Suitable oily excipients or solvents are, for example, vegetable or animal oils, such as sunflower oil or cod liver oil.

For subcutaneous or intravenous administration, the active compounds, if desired with the substances customary therefor such as solubilizers, emulsifiers or further auxiliaries, are brought into solution, suspension or emulsion. Possible solvents are, for example: water, physiological saline solution or alcohols, e.g. ethanol, propanol, glycerol, and in addition also sugar solutions such as glucose or mannitol solutions, or alternatively a mixture of the various solvents mentioned.

Suitable pharmaceutical formulations for administration in the form of aerosols or sprays are, for example, solutions, suspensions or emulsions of the active compound of the formula I in a pharmaceutically acceptable solvent, such as, in particular, ethanol or water, or a mixture of such solvents.

If required, the formulation can also contain other pharmaceutical auxiliaries such as surfactants, emulsifiers and stabilizers and also a propellant gas. Such a preparation contains the active compound customarily in a concentration from approximately 0.1 to 10, in particular from approximately 0.3 to 3, % by weight.

The dose of the active compound of a compound of the formula (I) to be administered and the frequency of administration depend on the potency and duration of action of the compounds used; additionally also on the nature and severity of the illness to be treated and on the sex, age, weight and individual responsiveness of the mammal to be treated. On average, the daily dose of a compound of the formula I in the case of a patient weighing approximately 75 kg is at least 0.001 mg/kg, preferably 0.01 mg/kg, to at most 10 mg/kg, preferably 1 mg/kg, of body weight. In the case of acute episodes of the illness, for example immediately after suffering a cardiac infarct, higher and especially more frequent doses may also be necessary, e.g. up to 4 individual doses per day. In particular in the case of i.v. administration, for example in the case of an infarct patient in the intensive care unit, up to 200 mg per day may be necessary.

The compounds of the formula I and/or their physiologically tolerable salts can also be employed to achieve an advantageous therapeutic action, together with other pharmacologically active compounds, for the treatment or prophylaxis of the abovementioned symptoms, in particular for the treatment of cardiovascular disorders. Combination with inhibitors of the sodium/hydrogen exchanger (NHE) and/or with active substances from other classes of cardiovascular active compound is preferred.

The invention additionally relates to the combination of a) NCBE inhibitors of the formula I and/or their physiologically tolerable salts with NHE inhibitors and/or their physiologically tolerable salts; b) NCBE inhibitors of the formula I and/or their physiologically tolerable salts with active substances from other classes of cardiovascular active compound and/or their physiologically tolerable salts and also c) of NCBE inhibitors of the formula I and/or their physiologically tolerable salts with NHE inhibitors and/or their physiologically tolerable salts and with active substances from other classes of cardiovascular active compound and/or their physiologically tolerable salts.

The active compounds which are known and identified as NHE inhibitors are guanidine derivatives, preferably acylguanidines, inter alia such as are described in Edward J. Cragoe, Jr., "DIURETICS, Chemistry, Pharmacology and Medicine", J. WILEY & Sons (1983), 303–341 or the NHE inhibitors mentioned in DE19737224.4.

Suitable NHE inhibitors are, for example, also benzoylguanidines such as are described in U.S. Pat. Nos. 5,292,755, 5,373,024, 5,364,868, 5,591,754, 5,516,805, 5,559,153, 5,571,842, 5,641,792, 5,631,293, EP-A 577024, EP-A 602522, EP-A 602523, EP-A 603650, EP-A 604852, EP-A 612723, EP-A 627413, EP-A 628543, EP-A 640593, EP-A 640588, EP-A 702001, EP-A 713864, EP-A 723956, EP-A 754680, EP-A 765868, EP-A 774459, EP-A 794171, EP-A 814077, EP-A 869116; ortho-substituted benzoylguanidines, such as are described in EP-A 556673, EP-A 791577, EP-A 794172; ortho-amino-substituted benzoylguanidines, such as are described in EP-A 690048; isoquinolines, such as are described in EP-A 590455; benzofused 5-membered ring heterocycles, such as are described in EP-A 639573; diacyl-substituted guanidines, such as are described in EP-A 640587; acylguanidines, such as are described in U.S. Pat. No. 5,547,953; phenyl-substituted alkyl- or alkenylcarboxylic acid guanidines bearing perfluoroalkyl groups, such as are described in U.S. Pat. No. 5,567,734, EP-A 688766; heteroaroylguanidines, such as are described in EP-A 676395; bicyclic heteroaroylguanidines, such as are described in EP-A 682017; indenoylguanidines, such as are described in EP-A 738712; benzyloxycarbonylguanidines, such as are described in EP-A 748795; phenyl-substituted alkenylcarboxylic acid guanidines bearing fluorophenyl groups, such as are described in EP-A 744397; substituted cinnamoylguanidines, such as are described in EP-A 755919; sulfonimidamides, such as are described in EP-A 771788; benzenedicarboxylic acid diguanidines, such as are described in EP-A 774458, EP-A 774457; diarylcarboxylic acid diguanidines, such as are described in EP-A 787717; substituted thiophenylalkenylcarboxylic acid guanidines, such as are described in EP-A 790245; bis-ortho-substituted benzoylguanidines, such as are described in EP-A 810207; substituted 1 or 2-naphthylguanidines, such as are described in EP-A 810205 and EP-A 810206; indanylideneacetylguanidines, such as are described in EP-A 837055; phenyl-substituted alkenylcarboxylic acid guanidines such as are described in EP-A 825178; aminopiperidylbenzoylguanidines, such as are described in EP-A 667341; heterocycloxybenzylguanidines, such as are described in EP-A 694537; ortho-substituted benzoylguanidines, such as are described in EP-A 704431; ortho-substituted alkylbenzylguanidines, such as are described in EP-A 699660; ortho-substituted heterocyclylbenzoylguanidines, such as are described in EP-A 699666; ortho-substituted 5-methylsulfonylbenzoylguanidines, such as are described in EP-A 708088; ortho-substituted 5-alkylsulfonylbenzoylguanidines having 4-amino substituents, such as are described in EP-A 723963; ortho-substituted 5-alkylsulfonylbenzoylguanidines having 4-mercapto substituents, such as are described in EP-A 743301; 4-sulfonyl or 4-sulfinylbenzylguanidines, such as are described in EP-A 758644; alkenylbenzoylguanidines, such as are described in EP-A 760365; benzoylguanidines having fused, cyclic sulfones, such as are described in DE 19548708; benzoyl-, polycyclic aroyl- and heteroaroylguanidines, such as are described in WO 9426709; 3-aryl/heteroarylbenzoylguanidines, such as are described in WO 9604241; 3-phenylbenzoylguanidines having a basic amide in the 5-position, such as are described in WO 9725310; 3-dihalothienyl- or 3-dihalophenylbenzoylguanidines having a basic substituent in the 5-position, such as are described in WO 9727183; 3-methylsulfonylbenzoylguanidines having certain amino substituents in the 4-position, such as are described in WO 9512584; amiloride derivatives, such as are described in WO 9512592; 3-methylsulfonyl-benzoylguanidines having certain amino substituents in the 4-position, such as are described in WO 9726253; indoloylguanidines, such as are described in EP-A 622356 and EP-A 708091; indoloylguanidines having a fused additional ring system, such as are described in EP 787728; methylguanidine derivatives, such as are described in WO 9504052; 1,4-benzoxazinoylguanidines, such as are described in EP-A 719766; 5-bromo-2-naphthoylguanidines, such as are described in JP 8225513; quinoline-4-carbonylguanidines having a phenyl radical in the 2-position, such as are described in EP-A 726254; cinnamoylguanidines, such as are described in JP 09059245; propenoylguanidines having a naphthalene substituent, such as are described in JP 9067332; propenoylguanidines having indole substituents, such as are described in JP 9067340; or heteroaryl-substituted acroylguanidines, such as are described in WO 9711055, and their physiologically tolerable salts.

Preferred NHE inhibitors are the compounds emphasized as preferred in the publications mentioned. Very particularly preferred compounds are cariporide (HOE642), HOE 694, EMD 96785, FR 168888, FR 183998, SM-20550, KBR-9032, and their physiologically tolerable salts. Most preferred is cariporide or another physiologically tolerable salt of N-(4-isopropyl-3-methanesulfonylbenzoyl)guanidine.

Examples of classes of active compounds having cardiovascular activity which can therapeutically be combined advantageously with NCBE inhibitors or can additionally be combined with combinations of NCBE inhibitors and NHE inhibitors are beta-receptor blockers, calcium antagonists, angiotensin-converting enzyme inhibitors, angiotensin receptor blockers, loop diuretics, thiazide diuretics, potassium-sparing diuretics, aldosterone antagonists, such as are employed, for example, in lowering of the blood pressure, and also cardiac glycosides or other agents increasing the contractile force in the treatment of cardiac insufficiency and of congestive heart failures, and also antiarrhythmics of the classes I–IV, nitrates, KATP openers, KATP blockers, inhibitors of the veratridine-activatable sodium channel, etc. For example, the following are thus suitable: the beta-blockers propanolol, atenolol, metoprolol; the calcium antagonists diltiazem hydrochloride, verapamil hydrochloride, nifedipine; the ACE inhibitors captopril, enalapril, ramipril; trandolapril, quinapril, spirapril, preferably ramipril or trandolapril; the angiotensin II receptor antagonists losartan, valsartan, telmisartan, eprosartan, tasosartan, candesartan, irbesartan; the loop diuretics furosemide, piretanide, torasemide; the thiazide diuretics hydrochlorothiazide, metolazone, indapamide; the potassium-sparing diuretics amiloride, triamterene, spironolactone; the cardiac glycosides digoxin, digitoxin, strophanthin; the antiarrhythmics amiodarone, sotalol, bretylium, flecainide; the nitrate glycerol trinitrate; the $K^+(ATP)$ openers cromakalim, lemakalim, nocorandil, pinacidil, minoxidil; the inhibitors of the veratridine-activatable $Na^+$ channel. An example of such a particularly advantageous combination component with NCBE inhibitors are blockers of the non-inactivating sodium channel (veratridine-activatable sodium channel). The combinations of an NCBE inhibitor with a blocker of the non-inactivating sodium channel (veratridineactivatable sodium channel) are suitable for infarct and reinfarct prophylaxis and infarct treatment and also for the treatment of angina pectoris and the inhibition of ischemically induced cardiac arrhythmias, tachycardia and the formation and maintenance of ventricular fibrillation, the combinations of an NCBE inhibitor with a blocker of the non-inactivating sodium channel also preventively inhibiting or greatly decreasing the pathophysiological processes in the formation of ischemically induced damage. Because of their enhanced protective actions against pathological hypoxic and ischemic situations, the combinations according to the invention of an NCBE inhibitor with a blocker of the non-inactivating sodium channel can be used, as a result of enhanced inhibition of the $Na^+$ influx into the cell, as pharmaceuticals for the treatment of all acute or chronic damage induced by ischemia or diseases induced primarily or secondarily thereby. This relates to their use as pharmaceuticals for surgical interventions, e.g. in organ transplantation, where the combinations of an NCBE inhibitor with a blocker of the non-inactivating sodium channel can be used both for the protection of the organs in the donor before and during removal, for the protection of removed organs, for example, also during storage thereof in physiological bath fluids, and also during transfer to the recipient's body. The combinations of an NCBE inhibitor with a blocker of the non-inactivating sodium channel are likewise valuable, protectively acting pharmaceuticals when carrying out angioplastic surgical interventions, for example on the heart, and also on peripheral vessels. In accordance with their protective action against ischemically induced damage, the combinations of an NCBE inhibitor with a blocker of the noninactivating sodium channel are also suitable as pharmaceuticals for the treatment of ischemias of the nervous system, in particular of the central nervous system, where they are suitable for the treatment of stroke or of cerebral edema. Moreover, the combinations according to the invention of an NCBE inhibitor with a blocker of the non-inactivating sodium channel are also suitable for the treatment of forms of shock, such as, for example, of allergic, cardiogenic, hypovolemic and bacterial shock.

Beside administration as a fixed combination, the invention also relates to the simultaneous, separate or sequential administration of NCBE inhibitors of the formula I and/or their physiologically tolerable salts with NHE inhibitors and/or an additional active substance from another class of cardiovascular active compound for the treatment of the abovementioned diseases.

The invention additionally relates to a pharmaceutical preparation comprising a) an NCBE inhibitor of the formula I and/or their physiologically tolerable salt and an NHE inhibitor and/or their physiologically tolerable salts; or b) an NCBE inhibitor of the formula I and/or their physiologically tolerable salt and additionally an active substance from another class of cardiovascular active compound and/or their physiologically tolerable salts; or c) an NCBE inhibitor of the formula I and/or its physiologically tolerable salt, an NHE inhibitor and additionally an active substance from another class of cardiovascular active compound, and/or its physiologically tolerable salts.

By combined administration, the effect of one combination component can be potentiated by the respective other component, i.e. the action and/or duration of action of a combination or preparation according to the invention is stronger or longer-lasting than the action and/or the duration of action of the respective individual components (synergistic effect). In the case of combined administration, this leads to a lowering of the dose of the respective combination components, compared with individual administration. The combinations and preparations according to the invention accordingly have the advantage that the amounts of active compound to be administered can be significantly reduced and undesirable side effects can be eliminated or greatly reduced.

The invention furthermore relates to a commercial pack, comprising as pharmaceutical active compound a) an NCBE inhibitor of the formula I and an NHE inhibitor and/or their physiologically tolerable salts; or b) an NCBE inhibitor of the formula I and additionally an active substance from another class of cardiovascular active compound and/or their physiologically tolerable salts; or c) an NCBE inhibitor of the formula I, an NHE inhibitor and additionally an active substance from another class of cardiovascular active compound and/or their physiologically tolerable salts, in each case together with instructions for the use of these active compounds in combination for simultaneous, separate or sequential administration in the treatment or prophylaxis of the abovementioned syndromes, in particular for the treatment of cardiovascular disorders.

The pharmaceutical preparations according to the invention can be prepared, for example, by either intensively mixing the individual components as powders, or by dissolving the individual components in the suitable solvents such as, for example, a lower alcohol and then removing the solvent.

The weight ratio of NBCE inhibitor to the NHE inhibitor or the substance having cardiovascular activity in the combinations and preparations according to the invention is expediently 1:0.01 to 1:100, preferably 1:0.1 to 1:10.

The combination and preparations according to the invention contain a total of preferably 0.5–99.5% by weight, in particular 4–99% by weight, of these active compounds.

When used according to the invention in mammals, preferably in humans, the doses of the various active compound components vary, for example, in the range from 0.001 to 100 mg/kg/day.

List of abbreviations:

| BCECF | 2',7'-Bis(2-carboxyethyl)-5,6-carboxyfluorescein |
| --- | --- |
| $CH_2Cl_2$ | Dichloromethane |
| DCI | Desorption-chemical ionization |
| DMF | N,N-Dimethylformamide |
| EA | Ethyl acetate (EtOAc) |
| EI | Electron impact |
| ES | Electrospray ionization |
| HEP | n-Heptane |
| MeOH | Methanol |
| mp | Melting point |
| NCBE | sodium-dependent chloride/bicarbonate exchanger |
| NHE | Sodium/hydrogen exchanger |
| RT | Room temperature |
| CNS | Central nervous system |

General Procedure for the Preparation of Sulfonylcyanamides from Sulfonamides

The sulfonamide starting material is dissolved in 10 ml/mmol of anhydrous acetonitrile, 3 mol equivalents of $K_2CO_3$ and one mol equivalent of a 5 N solution of BrCN in acetonitrile are added dropwise and the mixture is heated under reflux until conversion is complete (typical reaction time 10 minutes to 6 hours). The reaction mixture is then chromatographed on silica gel without further working up.

EXAMPLES

Example 1

4'-[5-Formyl-4-(2-methoxyethoxy)-2-phenylimidazol-1-ylmethyl]-3'-methanesulfonylbiphenyl-2-sulfonylcyanamide

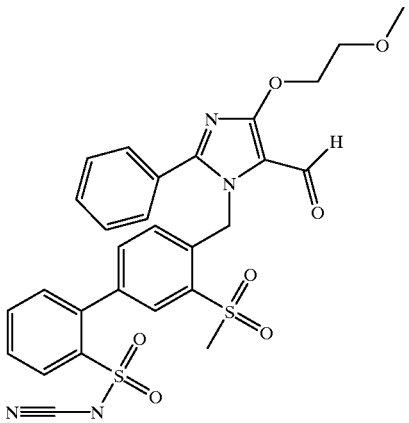

a) 2-Bromo-5-methylbenzenesulfonyl chloride 40 g of 4-bromotoluene are slowly introduced into 250 ml of chlorosulfonic acid at −10° C. with stirring. The mixture is stirred at this temperature for 30 minutes, allowed to warm to 0° C. and poured onto excess ice. The product is filtered off with suction and washed with a little water. It is dried over $P_4O_{10}$ in vacuo and 63 g of a colorless solid are obtained, which is directly reacted further.

b) 2-Bromo-5-methylbenzenesulfinic acid 37.6 g of sodium sulfite are dissolved in 500 ml of water and heated to 70° C. 62 g of 2-bromo-5-methylbenzenesulfonyl chloride are added in portions at this temperature. A 10 N aqueous NaOH solution is simultaneously added dropwise here so that the pH of the solution is kept between pH=9 and pH=10. The mixture is stirred at 70° C. for 1.5 hours, and the solution is filtered off and subsequently adjusted to pH=0 in an ice bath using a saturated aqeuous HCl solution. The mixture is stirred for 30 minutes, then the product is filtered off, subsequently washed with a little water and dried. 49.6 g of white crystals are obtained, mp 120–122° C. MS (ES): 236 (M+H)$^+$ c) Sodium 2-bromo-5-methylbenzenesulfinate 49.6 g of 2-bromo-5-methylbenzenesulfinic acid are dissolved in 400 ml of methanol and treated with an equimolar amount of NaOH in 50 ml of water. The mixture is stirred at RT for 3 hours, the solution is filtered off and subsequently the solvents are removed in vacuo. Finally, water residues are removed azeotropically with 50 ml of toluene. The solid residue is dried over $P_4O_{10}$ in vacuo and 54.0 g of product are obtained, mp 288–290° C. (with decomposition).

d) 1-Bromo-2-methanesulfonyl-4-methylbenzene 54.0 g of sodium 2-bromo-5-methylbenzenesulfinate are suspended in 300 ml of anhydrous DMF and treated with 45.7 ml of methyl iodide. The temperature of the solution rises to 50° C. in the course of this. The mixture is stirred at 50° C. for 3 hours and the DMF is removed in vacuo. The residue is stirred with 500 ml of water, subsequently stirred at 0° C. for 1 hour and filtered off. The product is washed with water, dried and recrystallized from 400 ml of HEP/250 ml of EA using active carbon. 27.0 g of colorless crystals are obtained, mp 110–114° C.

$R_f$(EA/HEP 1:4)=0.09 MS (DCI): 250 (M+H)$^+$ e) 1-Bromo-4-bromomethyl-2-methanesulfonylbenzene 9.9 g of 1-bromo-2-methanesulfonyl-4-methylbenzene are taken up in 100 ml of chlorobenzene, 77 mg of benzoyl peroxide and 7.1 g of N-bromosuccinimide are added and the mixture is refluxed for 1 hour. The solvent is then removed in vacuo, the residue is taken up in 100 ml of $CH_2Cl_2$ and the mixture is washed twice with 50 ml of a saturated aqueous $Na_2CO_3$ solution and once with 50 ml of water. It is dried over $Na_2SO_4$ and the solvent is removed in vacuo. The residue is recrystallized from 80 ml of HEP/30 ml of EA and 6.9 g of a pale yellow solid are obtained, mp 120–124° C.

$R_f$(EA/HEP 1:2)=0.38 MS (DCI): 329 (M+H)$^+$ f) 3-(4-Bromo-3-methanesulfonylbenzyl)-5-chloro-2-phenyl-3H-imidazole-4-carbaldehyde 1.0 g of 5-chloro-2-phenyl-3H-imidazole-4-carbaldehyde (Chem. Pharm. Bull. 1976, 24(5), 960), 1.6 g of 1-bromo-4-bromomethyl-2-methanesulfonylbenzene and 691 mg of $K_2CO_3$ are stirred at RT for 18 hours in 25 ml of anhydrous DMF. The reaction mixture is poured onto 300 ml of a semisaturated aqueous $NaHCO_3$ solution and extracted 3 times with 150 ml of EA each time. The extract is dried over $Na_2SO_4$ and the solvent is removed in vacuo. Chromatography on silica gel using EA/HEP 1:2 yields 1.2 g of a colorless oil.

$R_f$(EA/HEP 1:2)=0.16 MS (FAB): 454 (M+H)$^+$ g) 4'-(4-Chloro-5-formyl-2-phenylimidazol-1-ylmethyl)-3'-methanesulfonylbiphenyl-2-sulfonic acid tert-butylamide 970 mg of 3-(4-bromo-3-methanesulfonylbenzyl)-5-chloro-2-phenyl-3H-imidazole-4-carbaldehyde, 660 mg of N-tert-butyl-2-dihydroxyboran-2-ylbenzenesulfonamide (J. Med. Chem. 1997, 40, 547), 24 mg of Pd(II) acetate and 56 mg of triphenylphosphine are taken up in 13 ml of toluene and 3.5 ml of ethanol and 2.1 ml of an aqueous 2 M $Na_2CO_3$ solution are added. The reaction mixture is refluxed for 105 minutes, then allowed to cool to RT and taken up in 200 ml of a semisaturated aqueous $NaHCO_3$ solution. The mixture is extracted 3 times using 150 ml of EA each time, dried over $Na_2SO_4$ and the solvent is removed in vacuo. Chromatography on silica gel using EA/HEP 1:2 yields 660 mg of a colorless oil.

$R_f$(EA/HEP 1:2)=0.12 MS (ES): 587 (M+H)$^+$ h) 4'-(4-Chloro-5-formyl-2-phenylimidazol-1-ylmethyl)-3'-methanesulfonylbiphenyl-2-sulfonamide 650 mg of 4'-(4-chloro-5-formyl-2-phenylimidazol-1-ylmethyl)-3'-methanesulfonylbiphenyl-2-sulfonic acid tert-butylamide are dissolved in 5.6 ml of trifluoroacetic acid and 133 µl of anisole are injected. The mixture is stirred at RT for 8 hours, then the volatile constituents are removed in vacuo. The residue is again taken up in 20 ml of water 3 times and the water is then removed in vacuo. Finally, the residue is suspended 2 more times in 30 ml of toluene each time and the volatile constituents are again removed in vacuo. 570 mg of a pale yellow solid are obtained, which is reacted further without purification because of inadequate solubility.

$R_f$(EA/HEP 2:1)=0.24 i) 4'-[5-Formyl-4-(2-methoxyethoxy)-2-phenylimidazol-1-ylmethyl]-3'-methanesulfonylbiphenyl-2-sulfonamide 330 mg of 4'-(4-chloro-5-formyl-2-phenylimidazol-1-ylmethyl)-3'-methanesulfonylbiphenyl-2-sulfonamide and 250 mg of NaOH are stirred at 90° C. for 2 hours in 12.5 ml of methoxyethanol. The reaction mixture is subsequently cooled to RT and subsequently poured onto 100 ml of a semisaturated aqueous $NaHCO_3$ solution. It is extracted 3 times with 100 ml of EA each time, dried over $Na_2SO_4$ and the solvent is removed in vacuo. 350 mg of a colorless oil are obtained, which immediately has to be employed further without purification because of surprising instability.

$R_f$(EA/HEP 2:1)=0.18 j) 4'-[5-Formyl-4-(2-methoxyethoxy)-2-phenylimidazol-1-ylmethyl]-3'-methanesulfonylbiphenyl-2-sulfonylcyanamide 340 mg of 4'-[5-formyl-4-(2-methoxyethoxy)-2-phenylimidazol-1-ylmethyl]-3'-methanesulfonylbiphenyl-2-sulfonamide are reacted according to the general procedure for the preparation of sulfonylcyanamides from sulfonamides (reaction time 15 minutes) and, after chromatography on silica gel using EA/MeOH 1:5, 90 mg of white crystals are obtained, mp>270° C.

$R_f$(EA/MeOH 1:5)=0.27 IR (C≡N): 2178.1 cm$^{-1}$ MS (FAB): 595 (M+H)$^+$

Example 2

3'-Chloro-4'-[5-formyl-4-(2-methoxyethoxy)-2-phenylimidazol-1-ylmethyl]-biphenyl-2-sulfonylcyanamide

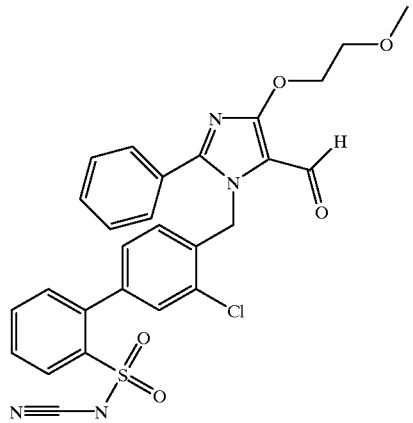

a) 4-Bromo-1-bromomethyl-2-chlorobenzene 7.1 ml of 4-bromo-2-chlorotoluene are dissolved in 20 ml of chlorobenzene and treated in portions at 130° C. with a mixture of 9.4 g of N-bromosuccinimide and 200 mg of dibenzoyl peroxide. The mixture is refluxed for 30 minutes, diluted with 100 ml of $CH_2Cl_2$ after cooling and washed once each with 50 ml of a saturated aqueous $Na_2SO_3$ solution and 100 ml of a saturated aqueous $NaHCO_3$ solution. It is dried over $Na_2SO_4$ and the solvent is removed in vacuo. 11.0 g of a pale yellow oil are obtained.

$R_f$(EA/HEP 1:8)=0.49 MS (DCI): 283 (M+H)$^+$ b) 3-(4-Bromo-2-chlorobenzyl)-5-chloro-2-phenyl-3H-imidazole-4-carbaldehyde 1.5 g of 4-chloro-5-formyl-2-phenylimidazole (Chem. Pharm. Bull. 1976, 24(5), 960), 5.8 g of $K_2CO_3$ and 8.0 g of 4-bromo-1-bromomethyl-2-chlorobenzene are stirred at RT for 24 h in 50 ml of DMF. The mixture is then diluted with 250 ml of EA and washed twice each with 100 ml of water and once with 100 ml of a saturated aqueous NaCl solution. It is dried over $Na_2SO_4$ and the solvents are removed in vacuo. Chromatography on silica gel using EA/HEP 1:4 yields 2.2 g of a colorless oil.

$R_f$(EA/HEP 1:4)=0.47 MS (ES): 411 (M+H)$^+$ c) 3'-Chloro-4'-(4-chloro-5-formyl-2-phenylimidazol-1-ylmethyl)biphenyl-2-sulfonic acid tert-butylamide 2.2 g of 3-(4-bromo-2-chlorobenzyl)-5-chloro-2-phenyl-3H-imidazole-4-carbaldehyde, 2.0 g of N-tert-butyl-2-dihydroxyboran-2-ylbenzenesulfonamide (J. Med. Chem. 1997, 40, 547), 140 mg of triphenylphosphine, 64 mg of Pd(II) acetate and 1.2 g of $Na_2CO_3$ are dissolved in 30 ml of toluene, 10 ml of ethanol and 10 ml of water and refluxed for 3 h. After cooling, 200 ml of a saturated aqueous $NaHCO_3$ solution are added and the mixture is extracted 3 times with 200 ml of EA each time. It is dried over $MgSO_4$ and the solvent is removed in vacuo. Chromatography on silica gel yields 1.5 g of a colorless foam.

$R_f$(DIP)=0.25 MS (ES): 542 (M+H)$^+$ d) 3'-Chloro-4'-(4-chloro-5-formyl-2-phenylimidazol-1-ylmethyl)biphenyl-2-sulfonamide 1.5 g of 3'-chloro-4'-(4-chloro-5-formyl-2-phenylimidazol-1-ylmethyl)biphenyl-2-sulfonic acid tert-butylamide and 340 μl of anisole are dissolved in 10 ml of trifluoroacetic acid and stirred at RT for 24 h. The volatile constituents are removed in vacuo, the residue is taken up twice with 50 ml of toluene each time and the volatile constituents are again removed in vacuo. 1.5 g of a colorless foam are obtained.

$R_f$(DIP)=0.15 MS (ES): 486 (M+H)$^+$ e) 3'-Chloro-4'-[5-formyl-4-(2-methoxyethoxy)-2-phenylimidazol-1-ylmethyl]biphenyl-2-sulfonamide 280 mg of 3'-chloro-4'-(4-chloro-5-formyl-2-phenylimidazol-1-ylmethyl)biphenyl-2-sulfonamide and 230 mg of NaOH are stirred at 90° C. for 3 hours in 11.5 ml of methoxyethanol. After cooling, the reaction mixture is taken up in 150 ml of a semisaturated aqueous $NaHCO_3$ solution and extracted 3 times using 100 ml of EA each time. The extract is dried over $Na_2SO_4$ and the solvent is removed in vacuo. 310 mg of a colorless oil are obtained, which is directly reacted further without purification.

$R_f$(EA/HEP 2:1)=0.37 f) 3'-Chloro-4'-[5-formyl-4-(2-methoxyethoxy)-2-phenylimidazol-1-ylmethyl]biphenyl-2-sulfonylcyanamide 69 mg of 3'-chloro-4'-[5-formyl-4-(2-methoxyethoxy)-2-phenylimidazol-1-ylmethyl]biphenyl-2-sulfonamide are reacted according to the general procedure for the preparation of sulfonylcyanamides from sulfonamides (reaction time 1 hour) and, after chromatography on silica gel using EA/MeOH 1:5, 63 mg of white crystals are obtained, mp 195° C. (with decomposition).

$R_f$(EA/MeOH 1:5)=0.33 IR (C≡N): 2178.6 cm$^{-1}$ MS (ES): 552 (M+H)$^+$

Example 3

4'-[5-Formyl-2-(4-isopropylphenyl)-4-(2-methoxyethoxy)imidazol-1-ylmethyl]biphenyl-2-sulfonylcyanamide

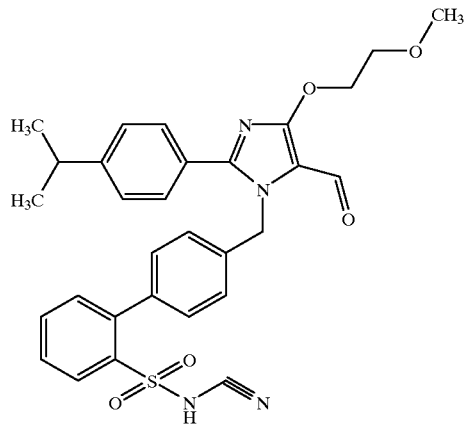

a) 4'-[4-Chloro-5-formyl-2-(4-isopropylphenyl)imidazol-1-ylmethyl]biphenyl-2-sulfonic acid dimethylaminomethylenamide 1.2 g of 5-chloro-2-(4-isopropylphenyl)-3H-imidazole-4-carbaldehyde (synthesized analogously to Chem. Pharm. Bull. 1976, 24(5), 960), 1.9 g of 4'-bromomethylbiphenyl-2-sulfonic acid dimethylaminomethylenamide and 0.69 g of $K_2CO_3$ are suspended in 25 ml of anhydrous DMF and stirred at RT for 8 hours. A further 0.38 g of 4'-bromomethylbiphenyl-2-sulfonic acid dimethylaminomethylenamide are added and the mixture is stirred at RT for a further 5 hours. The reaction mixture is diluted with 300 ml of a 10% aqueous $NaHCO_3$ solution and extracted 3 times using 150 ml of EA each time. The extract is dried over $Na_2SO_4$ and the solvent is removed in vacuo. Chromatography on silica gel using EA/HEP 2:1 yields 1.9 g of a colorless, crystalline solid, mp 177° C.

$R_f$(EA/HEP 2:1)=0.28 MS (ES): 550 (M+H)$^+$ b) 4'-[4-Chloro-5-formyl-2-(4-isopropylphenyl)imidazol-1-ylmethyl]biphenyl-2-sulfonamide 1.9 g of 4'-[4-chloro-5-formyl-2-(4-isopropylphenyl) imidazol-1-ylmethyl]biphenyl-2-sulfonic acid dimethylaminomethylenamide are dissolved in 35 ml of MeOH, 18 ml of a saturated aqueous HCl solution are added and the mixture is refluxed for 90 minutes. After cooling, it is adjusted to pH=5–6 using a 6N aqueous NaOH solution and the precipitated product is filtered off. It is washed 3 times with 20 ml of water each time and the product is dried at 60° C. in a fine vacuum. 1.4 g of an amorphous solid are obtained.

$R_f$(EA/HEP 1:1)=0.25 MS (ES): 495 (M+H)$^+$ c) 4'-[4-Chloro-5-formyl-2-(4-isopropylphenyl)imidazol-1-ylmethyl]biphenyl-2-sulfonylcyanamide 198 mg of 4'-[4-chloro-5-formyl-2-(4-isopropylphenyl) imidazol-1-ylmethyl]biphenyl-2-sulfonamide and 166 mg of $K_2CO_3$ are suspended in 2 ml of anhydrous acetonitrile and 80 μl of a 5N BrCN solution in acetonitrile are injected. The mixture is refluxed for one hour. After cooling, the entire reaction mixture is chromatographed on silica gel using EA/MeOH 5:1 and 170 mg of a crystalline solid are obtained, mp 217–218° C. (with decomposition).

$R_f$(EA/MeOH 5:1)=0.38 MS (ES): 520 (M+H)$^+$ d) 4'-[5-Formyl-2-(4-isopropylphenyl)-4-(2-methoxyethoxy)imidazol-1-ylmethyl]biphenyl-2-sulfonylcyanamide 140 mg of 4'-[4-chloro-5-formyl-2-(4-isopropylphenyl) imidazol-1-ylmethyl]biphenyl-2-sulfonylcyanamide and 108 mg of NaOH are dissolved in 5 ml of methoxyethanol and stirred at 90° C. for 105 minutes. After cooling, the mixture is taken up with 150 ml of a 10% aqueous NaHCO$_3$ solution and extracted 3 times using 100 ml of EA each time. It is dried over Na$_2$SO$_4$ and the solvent is removed in vacuo. Chromatography on silica gel using EA/MeOH 10:1 yields 90 mg of an amorphous solid.

R$_f$(EA/MeOH 10:1)=0.29 MS (ES): 559 (M+H)$^+$

Example 4

4'-[5-Formyl-4-(2-methoxyethoxy)-2-phenylimidazol-1-ylmethyl]-3'-(2-methoxyethoxy) biphenyl-2-sulfonylcyanamide

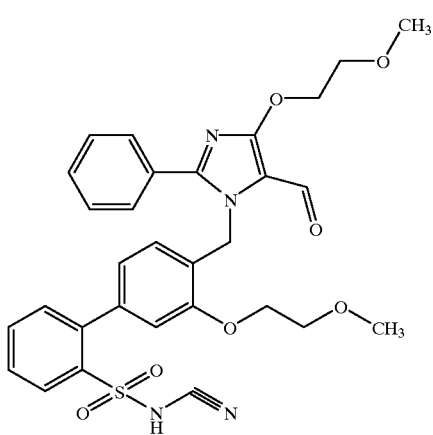

a) 4-Methyl-3-(2-methoxy)ethoxyaniline 22.0 g of 3-hydroxy-4-methylaniline, 24.9 g of 2-bromoethyl methyl ether and 233 g of Cs$_2$CO$_3$ are dissolved in 570 ml of DMF and stirred at 40° C. for 8 h. 3 of a 10% aqueous sodium hydrogencarbonate solution are added, the mixture is extracted 6 times using 750 ml of EA each time and washed twice using 1 of a 10% aqueous sodium hydrogencarbonate solution each time. It is dried over sodium sulfate and the solvent is removed in vacuo. 32.9 g of a yellow oil are obtained, which is employed further as such.

R$_f$(EA/HEP 1:1)=0.33 b) 4-Methyl-3-(2-methoxy)ethoxybromobenzene 32.8 g of 4-methyl-3-(2-methoxy)ethoxyaniline are suspended in 660 ml of a semisaturated aqueous HBr solution and a solution of 12.5 g of NaNO$_3$ in 25 ml of water is slowly added dropwise at 0° C. The mixture is subsequently stirred at 0° C. for 30 minutes and this solution is subsequently slowly added to a solution, heated to 50° C. of 51.9 g of CuBr in 490 ml of a saturated aqueous HBr solution. The reaction mixture is then slowly heated from 50° C. to 70° C. over a period of 6 h. After subsequent cooling, it is extracted 4 times using 500 ml of diethyl ether each time, washed with 500 ml of a saturated aqueous NaCl solution and dried over sodium sulfate. Chromatography on silica gel using EA/HEP 1:8 yields 15.4 g of a colorless oil.

R$_f$(EA/HEP 1:1)=0.41 MS (DCI): 245 (M+H)$^+$ c) 4-Bromomethyl-3-(2-methoxy)ethoxybromobenzene 15.3 g of 4-methyl-3-(2-methoxy)ethoxybromobenzene are dissolved in 300 ml of chlorobenzene and a mixture of 11.1 g of N-bromosuccinimide and 125 mg of benzoyl peroxide is added in portions under reflux. The mixture is refluxed for 24 h, the solvent is removed in vacuo and the residue is subsequently taken up with 500 ml of CH$_2$Cl$_2$. The mixture is washed first with 200 ml of a saturated aqueous Na$_2$SO$_4$ solution, then with 100 ml of a saturated aqueous sodium carbonate solution. It is dried over sodium sulfate and the solvent is removed in vacuo. Chromatography on silica gel using EA/HEP 1:15 yields 12.8 g of a pale yellow oil.

R$_f$(EA/HEP 1:4)=0.42 MS (DCI): 323 (M+H)$^+$ d) 3-[4-Bromo-2-(2-methoxyethoxy)benzyl]-5-chloro-2-phenyl-3H-imidazole-4-carbaldehyde 620 mg of 5-chloro-2-phenyl-3H-imidazole-4-carbaldehyde, 970 mg of 4-bromo-1-bromomethyl-2-(2-methoxyethoxy)benzene and 415 mg of K$_2$CO$_3$ are suspended in 15 ml of anhydrous DMF and stirred at RT for 15 hours. The mixture is taken up with 75 ml of a saturated aqueous Na$_2$CO$_3$ solution and 75 ml of water and extracted 3 times using 100 ml of EA each time. It is dried over Na$_2$SO$_4$ and the solvent is removed in vacuo. Chromatography on silica gel using EA/HEP 1:4 yields 640 mg of a colorless oil.

R$_f$(EA/HEP 1:2)=0.26 MS (ES): 450 (M+H)$^+$ e) 4'-(4-Chloro-5-formyl-2-phenylimidazol-1-ylmethyl)-3'-(2-methoxyethoxy)biphenyl-2-sulfonic acid tert-butylamide 620 mg of 3-[4-bromo-2-(2-methoxyethoxy)benzyl]-5-chloro-2-phenyl-3H-imidazole-4-carbaldehyde, 420 mg of 2-dihydroxyborylbenzenesulfonic acid tert-butylamide, 16 mg of Pd(II) acetate and 36 mg of triphenylphosphine are dissolved in 8 ml of toluene and 2 ml of ethanol and 1.4 ml of a 2N aqueous Na$_2$CO$_3$ solution are added. The reaction mixture is refluxed for 4 hours and, after cooling, it is diluted with 75 ml of a saturated aqueous Na$_2$CO$_3$ solution and 75 ml of water. It is extracted 3 times using 100 ml of EA each time. The extract is dried over Na$_2$SO$_4$ and the solvent is removed in vacuo. Chromatography on silica gel using EA/HEP 1:2 yields 600 mg of a colorless oil.

R$_f$(EA/HEP 1:2)=0.20 MS (ES): 583 (M+H)$^+$ f) 4'-(4-Chloro-5-formyl-2-phenylimidazol-1-ylmethyl)-3'-(2-methoxyethoxy)biphenyl-2-sulfonamide 570 mg of 4'-(4-chloro-5-formyl-2-phenylimidazol-1-ylmethyl)-3'-(2-methoxyethoxy)biphenyl-2-sulfonic acid tert-butylamide are dissolved in 5 ml of trifluoroacetic acid and 117 µl of anisole are added. The mixture is stirred at RT for 8 h, then the solvent is removed in vacuo. Chromatography on silica gel using EA/HEP 1:1 yields 350 mg of an amorphous solid.

R$_f$(EA/HEP 1:1)=0.27 MS (ES): 527 (M+H)$^+$ g) 4'-[5-Formyl-4-(2-methoxyethoxy)-2-phenylimidazol-1-ylmethyl]-3'-(2-methoxyethoxy)biphenyl-2-sulfonamide 340 mg of 4'-(4-chloro-5-formyl-2-phenylimidazol-1-ylmethyl)-3'-(2-methoxyethoxy)biphenyl-2-sulfonamide and 260 mg of NaOH are dissolved in 13 ml of 2-methoxyethanol and stirred at 90° C. for 7 hours. After cooling, the reaction mixture is diluted with 100 ml of a 10% aqueous NaHCO$_3$ solution and extracted 3 times using 100 ml of EA each time. The extract is dried over Na$_2$SO$_4$ and the solvent is removed in vacuo. Chromatography on silica gel using EA/HEP 2:1 yields 230 mg of an amorphous solid.

R$_f$(EA/HEP 2:1)=0.33 MS (ES): 566 (M+H)$^+$ h) 4'-[5-Formyl-4-(2-methoxyethoxy)-2-phenylimidazol-1-ylmethyl]-3'-(2-methoxyethoxy)biphenyl-2-sulfonylcyanamide 210 mg of 4'-[5-formyl-4-(2-methoxyethoxy)-2-phenylimidazol-1-ylmethyl]-3'-(2-methoxyethoxy) biphenyl-2-sulfonamide and 154 mg of K$_2$CO$_3$ are suspended in 4 ml of anhydrous acetonitrile and 74 µl of a 5N solution of BrCN in actonitrile are injected. The mixture is refluxed for 3 hours and, after cooling, the entire reaction mixture is chromatographed on silica gel using EA/MeOH 10:1. 170 mg of white crystals are obtained, mp 162° C.

$R_f$(EA/MeOH 10:1)=0.11 MS (ES): 591 (M+H)$^+$

Pharmacological Data

Inhibition of the Na$^+$-dependent Cl$^-$/HCO$_3^-$ Exchanger (NCBE) in Human Endothelial Cells Human endothelial cells (ECV-304) were detached from culture bottles with the aid of trypsin/EDTA buffer (0.05/0.02% in phosphate buffer) and, after centrifugation (100 g, 5 min), taken up in a buffered salt solution (mmol/l: 115 NaCl, 20 NH$_4$Cl, 5 KCl, 1 CaCl$_2$, 1 MgSO$_4$, 20 N-(2-hydroxyethyl)piperazine-N-2-ethanesulfonic acid (HEPES), 5 glucose and 1 g/l of bovine serum albumin; pH 7.4). This cell suspension was incubated at 37° C. for 20 min with 5 μM BCECF-acetoxymethyl ester. The cells were then washed and resuspended in a sodium- and bicarbonate-free buffer solution (mmol/l: 5 HEPES, 133.8 choline chloride, 4.7 KCl, 1.25 MgCl$_2$, 0.97 K$_2$HPO$_4$, 0.23 KH$_2$PO$_4$, 5 glucose; pH 7.4).

For subsequent fluorescence measurement in an FLIPR (Fluorescent Imaging Plate Reader) 100 μl of this cell suspension having 20,000 cells in each case were pipetted per well into a 96-well microtiter plate and this microtiter plate was centrifuged (100 g, 5 min).

In the FLIPR, 100 μl of buffer solution in each case were then removed from a further pretreated microtiter plate and pipetted into each of the 96 wells of the measurement plate. A bicarbonate- and sodium-containing buffer solution (mmol/l: 5 HEPES, 93.8 NaCl, 40 NaHCO$_3$, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) which contained 50 μM HOE 642 was used for a 100% control, i.e. a recovery of the intracellular pH (pH$_i$) via the NCBE. For a 0% control, i.e. no pH$_i$ recovery at all, a bicarbonate-free, sodium-containing buffer solution (mmol/l: 5 HEPES, 133.8 NaCl, 4.7 KCl, 1.25 CaCl$_2$, 1.25 MgCl$_2$, 0.97 Na$_2$HPO$_4$, 0.23 NaH$_2$PO$_4$, 5 glucose; pH 7.4) was employed, to which 50 μM HOE 642 were likewise added. The compounds according to the invention were added to the sodium- and bicarbonate-containing solution in various concentrations.

After addition of the buffer solutions to the dye-loaded, acidified cells in the measurement plate, the rise in the fluorescence intensity, which corresponded to a rise in the pH$_i$, in each well of the microtiter plate was determined. The kinetics were in this case recorded at 35° C. for a period of 2 minutes.

The increase in the fluorescence intensities for different concentrations of the compounds according to the invention was related to the two controls and from this the inhibitory action of the substances was determined.

Results

Residual activity of the NCBE at an inhibitor concentration of 10 μM (in %)

| Compound of Example No. | |
|---|---|
| 1 | 9.8 |
| 2 | 18.9 |
| 3 | 29.6 |
| 4 | 13.5 |

What is claimed is:

1. A compound of the formula I

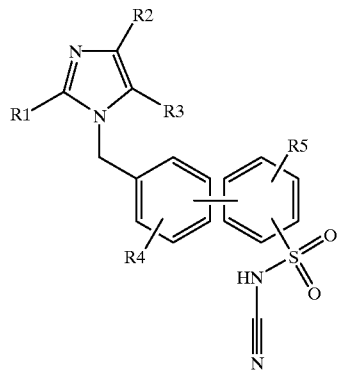

in which the symbols have the following meaning:

R(1) is hydrogen, alkyl having 1, 2, 3, 4, 5, 6, 7 or 8 carbon atoms or —C$_a$H$_{2a}$-phenyl, where the phenyl moiety is unsubstituted or substituted by 1, 2 or 3 identical or different radicals representing F, Cl, Br, I, CF$_3$, methyl, methoxy, hydroxyl or NR(8)R(9);

R(8) and R(9) independently of one another are hydrogen or alkyl having 1, 2, 3 or 4 carbon atoms;

a is zero, 1 or 2; or

R(1) is —C$_b$H$_{2b}$-heteroaryl having 1, 2, 3, 4, 5, 6, 7, 8 or 9 carbon atoms, where the heteroaryl moiety is unsubstituted or substituted by 1, 2 or 3 identical or different radicals representing F, Cl, Br, I, CF$_3$, methyl, methoxy, hydroxyl or NR(10)R(11);

R(10) and R(11) independently of one another are hydrogen or alkyl having 1, 2, 3 or 4 carbon atoms;

b is zero, 1 or 2; or

R(1) is —C$_d$H$_{2d}$-cycloalkyl having 3, 4, 5, 6 or 7 carbon atoms;

d is zero, 1 or 2;

R(2) and R(3) independently of one another are hydrogen, F, Cl, Br, I, CF$_3$, —CN, —NO$_2$, CH$_2$OR(17), CO—R(6), O—R(7), O-(alkylene having 2, 3 or 4 carbon atoms)-O—R(17) or NR(50)R(51);

R(17) is hydrogen or alkyl having 1, 2, 3, 4, 5, 6, 7 or 8 carbon atoms;

R(6) is hydrogen, alkyl having 1, 2, 3, 4, 5, 6, 7 or 8 carbon atoms, OR(30) or phenyl which is unsubstituted or substituted by 1, 2 or 3 identical or different radicals representing F, Cl, Br, I, CF$_3$, methyl, methoxy, hydroxyl or NR(31)R(32);

R(31) and R(32) independently of one another are hydrogen or alkyl having 1, 2, 3 or 4 carbon atoms;

R(30) is hydrogen or alkyl having 1, 2, 3, 4, 5, 6, 7 or 8 carbon atoms;

R(50) and R(51) independently of one another are -(alkylene having 2, 3 or 4 carbon atoms)-O—R(52);

R(52) is hydrogen or alkyl having 1, 2, 3, 4, 5, 6, 7, or 8 carbon atoms;

R(7) is hydrogen, alkyl having 1, 2, 3, 4, 5, 6, 7 or 8 carbon atoms, or phenyl, which is unsubstituted or substituted by 1, 2 or 3 identical or different radicals representing F, Cl, Br, I, CF$_3$, methyl, methoxy, hydroxyl or NR(12)R(13);

R(12) and R(13) independently of one another are hydrogen or alkyl having 1, 2, 3 or 4 carbon atoms; or R(7) is heteroaryl having 1, 2, 3, 4, 5, 6, 7, 8 or 9 carbon atoms, which is unsubstituted or substituted by 1, 2 or 3 identical or different radicals representing F, Cl, Br, I, $CF_3$, methyl, methoxy, hydroxyl or NR(14)R(15);

R(14) and R(15) independently of one another are hydrogen or alkyl having 1, 2, 3 or 4 carbon atoms; or R(2) and R(3) independently of one another are alkyl having 1, 2, 3, 4, 5, 6, 7 or 8 carbon atoms, cycloalkyl having 3, 4, 5, 6 or 7 carbon atoms or —$C_gH_{2g}$-phenyl, where the phenyl moiety is unsubstituted or substituted by 1, 2 or 3 identical or different radicals representing F, Cl, Br, I, $CF_3$, methyl, methoxy, hydroxyl or NR(18)R(19);

R(18) and R(19) independently of one another are hydrogen or alkyl having 1, 2, 3 or 4 carbon atoms;

g is zero, 1 or 2; or

R(2) and R(3) independently of one another are —$C_lH_{2l}$-heteroaryl having 1, 2, 3, 4, 5, 6, 7, 8 or 9 carbon atoms, where the heteroaryl moiety is unsubstituted or substituted by 1, 2 or 3 identical or different radicals representing F, Cl, Br, I, $CF_3$, methyl, methoxy, hydroxyl or NR(20)R(21);

R(20) and R(21) independently of one another are hydrogen or alkyl having 1, 2, 3 or 4 carbon atoms;

l is zero, 1 or 2; or

R(2) and R(3) independently of one another are $SO_n$—R(22);

n is zero, 1 or 2;

R(22) is alkyl having 1, 2, 3, 4, 5, 6, 7 or 8 carbon atoms, cycloalkyl having 3, 4, 5, 6 or 7 carbon atoms or —$C_sC_{2s}$-phenyl which is unsubstituted or substituted by 1, 2 or 3 identical or different radicals representing F, Cl, Br, I, $CF_3$, methyl, methoxy, hydroxyl or NR(34)R(35);

R(34) and R(35) independently of one another are hydrogen or alkyl having 1, 2, 3 or 4 carbon atoms;

s is zero, 1 or 2;

R(4) and R(5) independently of one another are hydrogen, alkyl having 1, 2, 3, 4, 5, 6, 7 or 8 carbon atoms, F, Cl, Br, I, $CF_3$, —CN, —$NO_2$, $SO_p$—R(16), CO—R(23), O—R(24) or O-(alkylene having 2, 3 or 4 carbon atoms)-O—R(33);

p is zero, 1 or 2;

R(16) is alkyl having 1, 2, 3, 4, 5, 6, 7 or 8 carbon atoms or phenyl, which is unsubstituted or substituted by 1, 2 or 3 identical or different radicals representing F, Cl, Br, I, $CF_3$, methyl, methoxy, hydroxyl or NR(26)R(27);

R(26) and R(27) independently of one another are hydrogen or alkyl having 1, 2, 3 or 4 carbon atoms;

R(23) is hydrogen, alkyl having 1, 2, 3, 4, 5, 6, 7 or 8 carbon atoms, or OR(25);

R(25) is hydrogen, alkyl having 1, 2, 3, 4, 5, 6, 7 or 8 carbon atoms;

R(24) is hydrogen, alkyl having 1, 2, 3, 4, 5, 6, 7 or 8 carbon atoms, or phenyl, which is unsubstituted or substituted by 1, 2 or 3 identical or different radicals representing F, Cl, Br, I, $CF_3$, methyl, methoxy, hydroxyl or NR(28)R(29);

R(28) and R(29) independently of one another are hydrogen or alkyl having 1, 2, 3 or 4 carbon atoms;

R(33) is hydrogen or alkyl having 1, 2, 3, 4, 5, 6, 7 or 8 carbon atoms;

or a physiologically tolerable salt thereof;

with the proviso that at least one of the radicals R(2) or R(3) is O-(alkylene having 2, 3 or 4 carbon atoms)-O—R(17) or NR(50)R(51).

2. A compound as claimed in claim 1, in which

R(1) is hydrogen, alkyl having 1, 2, 3 or 4 carbon atoms or —$C_aH_{2a}$-phenyl, where the phenyl moiety is unsubstituted or substituted by 1 or 2 identical or different radicals representing F, Cl, Br, $CF_3$, methyl, methoxy, hydroxyl or NR(8)R(9);

R(8) and R(9) independently of one another are hydrogen or methyl;

a is zero or 1; or

R(1) is heteroaryl having 1, 2, 3, 4, 5, 6, 7, 8 or 9 carbon atoms which is unsubstituted or substituted by a radical representing F, Cl, Br, $CF_3$, $CH_3$, methoxy, hydroxyl or NR(10)R(11);

R(10) and R(11) independently of one another are hydrogen or methyl; or

R(1) is —$C_dH_{2d}$-cycloalkyl having 3, 4, 5, 6 or 7 carbon atoms;

d is zero or 1;

R(2) and R(3) independently of one another are hydrogen, F, Cl, Br, $CF_3$, —CN, —$NO_2$, $CH_2OR(17)$, CO—R(6), O—R(7), O-(alkylene having 2 or 3 carbon atoms)-O—R(17) or NR(50)R(51);

R(17) is hydrogen or alkyl having 1, 2, 3 or 4 carbon atoms;

R(6) is hydrogen, alkyl having 1, 2, 3 or 4 carbon atoms, OR(30) or phenyl, which is unsubstituted or substituted by 1 or 2 identical or different radicals representing F, Cl, Br, $CF_3$, methyl, methoxy, hydroxyl or NR(31)R(32);

R(31) and R(32) independently of one another are hydrogen or methyl;

R(30) is hydrogen or alkyl having 1, 2, 3 or 4 carbon atoms;

R(7) is hydrogen, alkyl having 1, 2, 3 or 4 carbon atoms or phenyl, which is unsubstituted or substituted by 1 or 2 identical or different radicals representing F, Cl, Br, $CF_3$, methyl, methoxy, hydroxyl or NR(12)R(13);

R(12) and R(13) independently of one another are hydrogen or methyl; or

R(7) is heteroaryl having 1, 2, 3, 4, 5, 6, 7, 8 or 9 carbon atoms, which is unsubstituted or substituted by 1 or 2 identical or different radicals representing F, Cl, Br, $CF_3$, methyl, methoxy, hydroxyl or NR(14)R(15);

R(14) and R(15) independently of one another are hydrogen or methyl;

R(50) and R(51) independently of one another are -(alkylene having 2 or 3 carbon atoms)-O—R(52);

R(52) is hydrogen or alkyl having 1, 2, 3 or 4 carbon atoms; or

R(2) and R(3) independently of one another are alkyl having 1, 2, 3 or 4 carbon atoms, cycloalkyl having 3, 4, 5, 6 or 7 carbon atoms or —$C_gH_{2g}$-phenyl, where the phenyl moiety is unsubstituted or substituted by 1 or 2 identical or different radicals representing F, Cl, Br, $CF_3$, methyl, methoxy, hydroxyl or NR(18)R(19);

R(18) and R(19) independently of one another are hydrogen or methyl;

g is zero or 1; or

R(2) and R(3) independently of one another are heteroaryl having 1, 2, 3, 4, 5, 6, 7, 8 or 9 carbon atoms, which is unsubstituted or substituted by a radical representing F, Cl, Br, $CF_3$, methyl, methoxy, hydroxyl or NR(20)R(21);

R(20) and R(21) independently of one another are hydrogen or methyl; or

R(2) and R(3) independently of one another are $SO_n$—R(22), n is zero, 1 or 2;

R(22) is alkyl having 1, 2, 3 or 4 carbon atoms, cycloalkyl having 3, 4, 5, 6 or 7 carbon atoms or —$C_sH_{2s}$-phenyl, where the phenyl moiety is unsubstituted or substituted by 1 or 2 identical or different radicals representing F, Cl, Br, $CF_3$, methyl, methoxy, hydroxyl or NR(34)R(35);

R(34) and R(35) independently of one another are hydrogen or methyl;

s is zero or 1;

R(4) and R(5) independently of one another are hydrogen, alkyl having 1, 2, 3 or 4 carbon atoms, F, Cl, Br, $CF_3$, —CN, —$NO_2$, $SO_p$—R(16), CO—R(23), O—R(24) or O-(alkylene having 2 or 3 carbon atoms)-O—R(33);

p is zero, 1 or 2;

R(16) is alkyl having 1, 2, 3 or 4 carbon atoms or phenyl, which is unsubstituted or substituted by 1 or 2 identical or different radicals representing F, Cl, Br, $CF_3$, methyl, methoxy, hydroxyl or NR(26)R(27);

R(26) and R(27) independently of one another are hydrogen or methyl;

R(23) is hydrogen, alkyl having 1, 2, 3 or 4 carbon atoms, or OR(25);

R(25) is hydrogen, alkyl having 1, 2, 3 or 4 carbon atoms;

R(24) is hydrogen, alkyl having 1, 2, 3 or 4 carbon atoms, or phenyl, which is unsubstituted or substituted by 1 or 2 identical or different radicals representing F, Cl, Br, $CF_3$, methyl, methoxy, hydroxyl or NR(28)R(29);

R(28) and R(29) independently of one another are hydrogen or methyl;

R(33) is hydrogen or alkyl having 1, 2, 3 or 4 carbon atoms;

with the proviso that at least one of the radicals R(2) or R(3) is O-(alkylene having 2 or 3 carbon atoms)-O—R(17) or NR(50)R(51).

3. A compound as claimed in claim 1, in which:

R(1) is hydrogen, alkyl having 1, 2, 3 or 4 carbon atoms or phenyl, which is unsubstituted or substituted by a radical representing F, Cl, Br, $CF_3$, methyl, methoxy, hydroxyl or NR(8)R(9);

R(8) and R(9) independently of one another are hydrogen or methyl; or

R(1) is heteroaryl having 1, 2, 3, 4, 5, 6, 7, 8 or 9 carbon atoms, which is unsubstituted or substituted by a radical representing F, Cl, Br, $CF_3$, methyl, methoxy, hydroxyl or NR(10)R(11);

R(10) and R(11) independently of one another are hydrogen or methyl; or

R(1) is cycloalkyl having 3, 4, 5, 6 or 7 carbon atoms;

R(2) and R(3) independently of one another are hydrogen, F, Cl, Br, $CF_3$, —CN, —$NO_2$, CO—R(6) or O—R(7), O—$CH_2$—$CH_2$—O—R(17) or NR(50)R(51);

R(6) is hydrogen, alkyl having 1, 2, 3 or 4 carbon atoms, OR(30) or phenyl, which is unsubstituted or substituted by a radical representing F, Cl, Br, $CF_3$, methyl, methoxy, hydroxyl or NR(31)R(32);

R(31) and R(32) independently of one another are hydrogen or methyl;

R(30) is hydrogen or alkyl having 1, 2 or 3 carbon atoms;

R(7) is hydrogen, alkyl having 1, 2, 3 or 4 carbon atoms or phenyl, which is unsubstituted or substituted by a radical representing F, Cl, Br, methyl, methoxy, hydroxyl or NR(12)R(13);

R(12) and R(13) independently of one another are hydrogen or methyl; or

R(7) is heteroaryl having 1, 2, 3, 4, 5, 6, 7, 8 or 9 carbon atoms, which is unsubstituted or substituted by a radical representing F, Cl, Br, $CF_3$, methyl, methoxy, hydroxyl or NR(14)R(15);

R(14) and R(15) independently of one another are hydrogen or methyl;

R(17) is methyl or ethyl;

R(50) and R(51) independently of one another are —$CH_2$—$CH_2$—O—R(52);

R(52) is methyl or ethyl; or

R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a radical representing F, Cl, Br, $CF_3$, methyl, methoxy, hydroxyl or NR(18)R(19);

R(18) and R(19) independently of one another are hydrogen or methyl; or

R(2) and R(3) independently of one another are heteroaryl having 1, 2, 3, 4, 5, 6, 7, 8 or 9 carbon atoms, which is unsubstituted or substituted by a radical representing F, Cl, Br, $CF_3$, $CH_3$, methoxy, hydroxyl or NR(20)R(21);

R(20) and R(21) independently of one another are hydrogen or methyl; or

R(2) and R(3) independently of one another are $SO_n$—R(22);

n is zero or 2;

R(22) is alkyl having 1, 2, 3 or 4 carbon atoms, cycloalkyl having 3, 4, 5, 6 or 7 carbon atoms or phenyl which is unsubstituted or substituted by 1 or 2 identical or different radicals representing F, Cl, Br, $CF_3$, methyl, methoxy, hydroxyl or NR(34)R(35);

R(34) and R(35) independently of one another are hydrogen or methyl;

R(4) and R(5) independently of one another are hydrogen, alkyl having 1, 2, 3 or 4 carbon atoms, F, Cl, $CF_3$, —CN, —$NO_2$, $SO_p$—R(16), CO—R(23), O—R(24) or O—$CH_2$—$CH_2$—O—R(33);

p is zero or 2;

R(23) is hydrogen, alkyl having 1, 2, 3 or 4 carbon atoms or OR(25);

R(25) is hydrogen, alkyl having 1, 2 or 3 carbon atoms;

R(24) is hydrogen, alkyl having 1, 2 or 3 carbon atoms or phenyl, which is unsubstituted or substituted by a radical representing F, Cl, Br, $CF_3$, methyl, methoxy, hydroxyl or NR(28)R(29);

R(28) and R(29) independently of one another are hydrogen or methyl;

R(16) is alkyl having 1, 2, 3 or 4 carbon atoms or phenyl which is unsubstituted or substituted by a radical representing F, Cl, Br, $CF_3$, methyl, methoxy, hydroxyl or NR(26)R(27);

R(26) and R(27) independently of one another are hydrogen or methyl;

R(33) is methyl or ethyl;

with the proviso that at least one of the radicals R(2) or R(3) is O—$CH_2$—$CH_2$—O—R(17) or NR(50)R(51).

4. A compound as claimed in claim 1, in which:

R(1) is alkyl having 1, 2, 3 or 4 carbon atoms or phenyl which is unsubstituted or substituted by a radical representing F, Cl, $CF_3$, methyl or methoxy; or R(1) is heteroaryl having 1, 2, 3, 4, 5, 6, 7, 8 or 9 carbon atoms, which is unsubstituted or substituted by a radical representing F, Cl, $CF_3$, methyl or methoxy; or R(1) is cycloalkyl having 3, 4, 5, 6 or 7 carbon atoms;

R(2) and R(3) independently of one another are hydrogen, F, Cl, $CF_3$, —CN, CO—R(6), O—R(7), O—$CH_2$—$CH_2$—O—$CH_3$ or NR(50)R(51);
  R(6) is hydrogen, alkyl having 1, 2, 3 or 4 carbon atoms, OR(30) or phenyl, which is unsubstituted or substituted by a radical representing F, Cl, $CF_3$, methyl or methoxy;
  R(30) is hydrogen, methyl or ethyl;
  R(7) is hydrogen, alkyl having 1, 2, 3 or 4 carbon atoms or phenyl, which is unsubstituted or substituted by a radical representing F, Cl, $CF_3$, methyl or methoxy; or
  R(7) is heteroaryl having 1, 2, 3, 4, 5, 6, 7, 8 or 9 carbon atoms, which is unsubstituted or substituted by a radical representing F, Cl, Br, $CF_3$, methyl or methoxy;
  R(50) and R(51) are —$CH_2$—$CH_2$—O—$CH_3$; or R(2) and R(3) independently of one another are alkyl having 1, 2, 3 or 4 carbon atoms, cycloalkyl having 3, 4, 5, 6 or 7 carbon atoms or phenyl, which is unsubstituted or substituted by a radical representing F, Cl, $CF_3$, methyl or methoxy; or R(2) and R(3) independently of one another are heteroaryl having 1, 2, 3, 4, 5, 6, 7, 8 or 9 carbon atoms, which is unsubstituted or substituted by a radical representing F, Cl, $CF_3$, methyl or methoxy; or R(2) and R(3) independently of one another are $SO_n$—R(22);
  n is zero or 2;
  R(22) is alkyl having 1, 2, 3 or 4 carbon atoms or phenyl which is unsubstituted or substituted by 1 or 2 identical or different radicals representing F, Cl, $CF_3$, methyl or methoxy;

R(4) and R(5) independently of one another are hydrogen, methyl, F, Cl, $CF_3$, —CN, $SO_2$—R(16), CO—R(23), O—R(24) or O—$CH_2$—$CH_2$—O—$CH_3$;
  R(16) is alkyl having 1, 2, 3 or 4 carbon atoms or phenyl which is unsubstituted or substituted by a radical representing F, Cl, $CF_3$, methyl or methoxy;
  R(23) is hydrogen, methyl or OR(25);
  R(25) is hydrogen, methyl or ethyl;
  R(24) is hydrogen, alkyl having 1, 2, 3 or 4 carbon atoms or phenyl, which is unsubstituted or substituted by a radical representing F, Cl, $CF_3$, methyl or methoxy;

with the proviso that at least one of the radicals R(2) or R(3) is O—$CH_2$—$CH_2$—O—$CH_3$ or NR(50)R(51).

5. A compound as claimed in claim 1, in which

R(1) is alkyl having 1, 2, 3, 4, 5, 6, 7 or 8 carbon atoms, —$C_dH_{2d}$-cycloalkyl having 3, 4, 5, 6 or 7 carbon atoms where d is equal to zero, 1 or 2 or —$C_aH_{2a}$-phenyl, where the phenyl moiety is unsubstituted or substituted by 1, 2 or 3 identical or different radicals representing F, Cl, Br, I, $CF_3$, methyl, methoxy, hydroxyl or NR(8)R(9);
  R(8) and R(9) independently of one another are hydrogen or alkyl having 1, 2, 3 or 4 carbon atoms;
  a is zero, 1 or 2;

R(2) is O-(alkylene having 2, 3 or 4 carbon atoms)-O—R(17) or NR(50)R(51);
  R(17) is hydrogen, alkyl having 1, 2, 3, 4, 5, 6, 7 or 8 carbon atoms,
  R(50) and R(51) independently of one another are -(alkylene 2, 3 or 4 carbon atoms)-O—R(52);
  R(52) is hydrogen or alkyl having 1, 2, 3, 4, 5, 6, 7 or 8 carbon atoms;

R(3) is hydrogen, —CN or CO—R(6);
  R(6) is hydrogen, alkyl having 1, 2, 3, 4, 5, 6, 7 or 8 carbon atoms or OR(30)
  R(30) is hydrogen or alkyl having 1, 2, 3, 4, 5, 6, 7 or 8 carbon atoms;

R(4) is hydrogen, Cl, F, Br, I, $SO_p$—R(16) or O—$CH_2$—$CH_2$—O—R(33);
  p is zero, 1 or 2;
  R(16) is alkyl having 1, 2, 3, 4, 5, 6, 7 or 8 carbon atoms or phenyl which is unsubstituted or substituted by 1, 2 or 3 identical or different radicals representing F, Cl, Br, I, $CF_3$, methyl, methoxy, hydroxyl or NR(26)R(27);
  R(26) and R(27) independently of one another are hydrogen or alkyl having 1, 2, 3 or 4 carbon atoms;
  R(33) is methyl or ethyl;

R(5) is hydrogen.

6. A compound as claimed in claim 1, in which:

R(1) is —$C_aH_{2a}$-phenyl, where the phenyl moiety is unsubstituted or substituted by 1 or 2 identical or different radicals representing F, Cl, Br, $CF_3$, methyl, methoxy, hydroxyl or NR(8)R(9);
  R(8) and R(9) independently of one another are hydrogen or methyl;
  a is zero or 1;

R(2) is O-(alkylene having 2, 3 or 4 carbon atoms)-O—R(17) or NR(50)R(51);
  R(17) is alkyl having 1, 2, 3 or 4 carbon atoms;
  R(50) and R(51) independently of one another are -(alkylene having 2, 3 or 4 carbon atoms)-O—R(52);
  R(52) is alkyl having 1, 2, 3 or 4 carbon atoms;

R(3) is CO—R(6);
  R(6) is hydrogen;

R(4) is $SO_2$R(16) where R(16) is alkyl having 1, 2, 3 or 4 carbon atoms; or O—$CH_2$—$CH_2$—O—$CH_3$;

R(5) is hydrogen.

7. A compound as claimed in claim 1, in which R(2) is O—$CH_2$—$CH_2$—O—R(17) or NR(50)R(51) where R(17) is equal to alkyl having 1, 2, 3 or 4 carbon atoms and R(50) and R(51) are equal to —$CH_2$—$CH_2$—O—R(52) where R(52) is equal to alkyl having 1, 2, 3 or 4 carbon atoms.

8. A pharmaceutical preparation, which comprises an effective amount of at least one compound as claimed in claim 1 and at least one pharmaceutical vehicle or excipient.

9. A pharmaceutical preparation as claimed in claim 8, which further comprises an effective amount of at least one NHE inhibitor and/or other active substance from another class of cardiovascular active compound, or a physiologically tolerable salt thereof.

10. A method for inhibiting the sodium-dependent bicarbonate/chloride exchanger in a host, which comprises administering to the host an effective amount of at least one compound as claimed in claim 1.

11. A method for the treatment or prophylaxis of cardiac infarct; angina pectoris; an illness caused by an ischemic condition; disturbed respiratory drive; an ischemic condition of the heart or of the peripheral or central nervous system; a stroke; an ischemic condition of a peripheral organ or limb; or an illness in which cell proliferation is a primary or secondary cause, which comprises administering to a host in need of the therapy or prophylaxis an effective amount of at least one compound as claimed in claim 1.

12. A method for the treatment of a state of shock, which comprises administering to a host in need of the treatment an effective amount of at least one compound as claimed in claim 1.

13. A method for the preservation or storage of an organ, which comprises contacting the organ with an effective amount of at least one compound as claimed in claim 1.

14. A method for the treatment of atherosclerosis, a late diabetic complication, a carcinomatous disorder, a fibrotic disorder, organ hypertrophy, hyperplasia, or a combination of two or more of the above, which comprises administering to a host in need of the treatment an effective amount of at least one compound as claimed in claim 1.

15. A method for the treatment or prophylaxis of cardiac infarct; angina pectoris; an illness caused by an ischemic condition; disturbed respiratory drive; an ischemic condition of the heart or of the peripheral or central nervous system; a stroke; an ischemic condition of a peripheral organ or limb; or an illness in which cell proliferation is a primary or secondary cause, which comprises administering to a host in need of the therapy or prophylaxis an effective amount of a pharmaceutical preparation as claimed in claim 8.

16. A method for the treatment of a state of shock, which comprises administering to a host in need of the treatment an effective amount of a pharmaceutical preparation as claimed in claim 8.

17. A method for the preservation or storage of an organ, which comprises contacting the organ with an effective amount of a pharmaceutical preparation as claimed in claim 8.

18. A method for the treatment of atherosclerosis, a late diabetic complication, a carcinomatous disorder, a fibrotic disorder, organ hypertrophy, hyperplasia, or a combination of two or more of the above, which comprises administering to a host in need of the treatment an effective amount of a pharmaceutical preparation as claimed in claim 8.

* * * * *